(12) United States Patent
Okandan et al.

(10) Patent No.: US 7,127,301 B1
(45) Date of Patent: Oct. 24, 2006

(54) FLEXIBLE RETINAL ELECTRODE ARRAY

(75) Inventors: Murat Okandan, Albuquerque, NM (US); Kurt O. Wessendorf, Albuquerque, NM (US); Todd R. Christenson, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 618 days.

(21) Appl. No.: 10/426,152

(22) Filed: Apr. 28, 2003

(51) Int. Cl.
*A61N 1/05* (2006.01)
(52) U.S. Cl. .......................................... 607/116; 607/54
(58) Field of Classification Search ..................... None
See application file for complete search history.

(56) References Cited

U.S. PATENT DOCUMENTS

| | | | |
|---|---|---|---|
| 3,342,754 A | 9/1967 | Gorham ........................ 260/2 |
| 5,016,633 A | 5/1991 | Chow ..................... 128/419 R |
| 5,024,223 A | 6/1991 | Chow ..................... 128/419 R |
| 5,215,088 A * | 6/1993 | Normann et al. ........... 600/377 |
| 5,476,494 A | 12/1995 | Edell .......................... 607/116 |
| 5,501,893 A | 3/1996 | Laermer ..................... 428/161 |
| 5,556,423 A | 9/1996 | Chow .......................... 607/54 |
| 5,575,813 A | 11/1996 | Edell .......................... 607/116 |
| 5,836,996 A | 11/1998 | Doorish ....................... 607/54 |
| 5,865,839 A | 2/1999 | Doorish ....................... 607/54 |
| 5,935,155 A | 8/1999 | Humayun ..................... 607/54 |
| 6,165,192 A | 12/2000 | Greenberg ................... 606/185 |
| 6,230,057 B1 | 5/2001 | Chow .......................... 607/54 |
| 6,324,429 B1 | 11/2001 | Shire .......................... 607/54 |
| 6,389,317 B1 | 5/2002 | Chow .......................... 607/54 |
| 6,393,327 B1 | 5/2002 | Scribner ...................... 607/54 |
| 6,507,758 B1 | 1/2003 | Greenberg .................... 607/54 |
| 6,533,798 B1 * | 3/2003 | Greenberg et al. .......... 606/185 |
| 7,027,874 B1 * | 4/2006 | Sawan et al. ................ 607/116 |
| 2002/0042638 A1 | 4/2002 | Iezzi ............................ 607/88 |
| 2002/0091421 A1 | 7/2002 | Greenberg .................... 607/54 |
| 2002/0099420 A1 | 7/2002 | Chow .......................... 607/54 |
| 2002/0111655 A1 | 8/2002 | Scribner ....................... 607/54 |
| 2002/0161417 A1 | 10/2002 | Scribner ....................... 607/54 |
| 2002/0193845 A1 | 12/2002 | Greenberg .................... 607/54 |
| 2003/0014089 A1 | 1/2003 | Chow .......................... 607/54 |
| 2003/0028225 A1 | 2/2003 | Chow .......................... 607/54 |

OTHER PUBLICATIONS

J. Wyatt and J. Rizzo, "Occular Implants for the Blind," *IEEE Spectrum*, pp. 47-53, May 1996.
M.S. Humayun, E. de Juan, Jr., J.D. Weiland, G. Dagnelie, S. Katona, R. Greenberg and S. Suzuki, "Pattern Electrical Stimulation of the Human Retina," *Vision Research*, vol. 39, pp. 2569-2576, 1999.

(Continued)

*Primary Examiner*—Robert E. Pezzuto
*Assistant Examiner*—Kristen Mullen
(74) *Attorney, Agent, or Firm*—John P. Hohimer

(57) ABSTRACT

An electrode array which has applications for neural stimulation and sensing. The electrode array can include a large number of electrodes each of which is flexibly attached to a common substrate using a plurality of springs to allow the electrodes to move independently. The electrode array can be formed from a combination of bulk and surface micromachining, with electrode tips that can include an electroplated metal (e.g. platinum, iridium, gold or titanium) or a metal oxide (e.g. iridium oxide) for biocompatibility. The electrode array can be used to form a part of a neural prosthesis, and is particularly well adapted for use in an implantable retinal prosthesis where the electrodes can be tailored to provide a uniform gentle contact pressure with optional sensing of this contact pressure at one or more of the electrodes.

46 Claims, 17 Drawing Sheets

Section 1 - 1

OTHER PUBLICATIONS

M. Schwarz, L. Ewe, R. Hauschild, B.J. Hosticka, J. Huppertz, S. Kolnsbert, W. Mokwa and H.K. Trieu, "Single Chip CMOS Imagers and Flexible Microelectronic Stimulators for a Retina Implant System," *Sensors and Actuators*, vol. 83, pp. 40-46, 2000.

M. Okandan, J. Jessing, T. Christenson, K. Wessendorf, M. Baker, P. Galambos and R. Myers, "Micromachined Conformal Electrode Array for Retinal Prosthesis Application," presented at the 2nd Annual IEEE-EMBS Special Topic Conference on Microtechnologies in Medicine and Biology, Madison, Wisconsin, May 2-4, 2002.

* cited by examiner

Section 2 - 2

FLEXIBLE RETINAL ELECTRODE ARRAY

GOVERNMENT RIGHTS

This invention was made with Government support under Contract No. DE-AC04-94AL85000 awarded by the U.S. Department of Energy. The Government has certain rights in the invention.

FIELD OF THE INVENTION

The present invention relates in general to electrode arrays, and in particular to a micromachined electrode array for interfacing with neural tissue that has applications for use in prosthetic devices including an implantable retinal prosthesis.

BACKGROUND OF THE INVENTION

Efforts are currently underway in a number of groups worldwide to develop an implantable retinal prosthesis to restore at least partial sight to persons suffering from certain forms of blindness due to end-stage photoreceptor degenerative diseases such as age-related macular degeneration and hereditary retinitis pigmentosa. Such retinal prostheses, which are currently being developed, are based on the electronic transfer of visual information from a camera located in front of the eye to receiver circuitry which will be implanted within the eye to feed the visual information in pixelized form an electrode array that will be placed either in front of the retina (epiretinal) or beneath the retinal tissue (sub-retinal). Electrical currents from the electrode array will then provide artificial stimulation of neural tissue (e.g. ganglion cells) in the retina to generate the visual perception of dots of light corresponding to the pixelized visual image, with the goal of being able to restore a measure of sight to a blind person. Further details of implantable retinal prostheses to which the electrode array of the present invention can be applied can be found, for example, in U.S. Pat. Nos. 5,476,494; 5,836,996; 5,935,155; and 6,393,327 which are all incorporated herein by reference; and in an article by John Wyatt et al. entitled "Occular Implants for the Blind" published in *IEEE Spectrum*, pp. 47–53, May 1996; in another article by Mark S. Humayun et al. entitled "Pattern Electrical Stimulation of the Human Retina" published in *Vision Research*, vol. 39, pp. 2569–2576, 1999; and in yet another article by M. Schwarz et al. entitled "Single Chip CMOS Imagers and Flexible Microelectronic Stimulators for a Retinal Implant System" published in *Sensors and Actuators*, vol. 83, pp. 40–46, 2000.

Although progress has been made in the development of retinal prostheses, there still remains a need for an improved electrode array which can provide from hundreds to tens of thousands or more individual electrodes, each of which can conform to the curvature of the retina while providing a gentle, uniform contact pressure on the retina to prevent damage to the underlying neural cells.

The present invention represents an advance in the art by providing a micromachined electrode array which comprises a plurality of spaced-apart electrodes, each of which is flexibly attached to a supporting substrate by a plurality of springs to allow independent movement of the individual electrodes, and to allow a spring constant of each spring to be tailored during design so that each electrode will provide substantially the same low contact force when urged into contact with the curved surface of the retina.

The micromachined electrode array of the present invention can also be adapted for neural stimulation or sensing applications for many different types of neural tissue including neural tissue associated with visual, auditory and sensory systems, and for neural tissue associated with the control of muscles (e.g. for bladder function or the activation of paretic limbs).

In certain embodiments of the present invention, the electrode array can be used to sense the contact force of one or more electrodes in contact with a neural surface to ensure that the contact force does not exceed a predetermined limit, or to ensure that the contact force provided by the electrodes is substantially the same.

These and other advantages of the present invention will become evident to those skilled in the art.

SUMMARY OF THE INVENTION

The present invention relates to a micromachined electrode array comprising a plurality of spaced-apart electrodes attached to a supporting substrate and protruding outward substantially normal to a surface of the substrate, with each electrode being flexibly attached at one end thereof to the substrate by a plurality springs. The substrate preferably comprises a semiconductor material (e.g. silicon); and the electrodes are formed, at least in part, from the semiconductor material and can further comprise a portion (e.g. an electrode tip or an overcoating) formed from a metal (e.g. platinum, titanium, gold, iridium or a combination thereof), or an electrically-conducting metal oxide (e.g. iridium oxide). A majority of each electrode can further be overcoated with an electrically-insulating material (e.g. parylene, silicon nitride, silicon dioxide or a combination thereof). Each electrode in the array can be moveable over a distance that is generally up to about 500 microns.

In the electrode array of the present invention, the springs can comprise folded or curved springs. In certain embodiments of the present invention (e.g. for use in contacting a substantially-planar surface), a spring constant of each spring in the electrode array can be made to be substantially the same; whereas in other embodiments of the present invention (e.g. for use in a retinal prosthesis), the spring constant of the springs attached to one electrode can be made different from the spring constant of the springs attached to another electrode. By tailoring the spring constant to be different for different electrodes in the array, each electrode can be made to provide a contact force that is substantially the same (i.e. uniform) when the electrode array is urged into contact with a curved surface such as that presented by the retina.

The electrode array can further comprise wiring on the substrate for electrically addressing each electrode. Additionally, in certain embodiments of the present invention, the electrode array can further include means for sensing a contact force for at least one of the plurality of electrodes when the electrode array is urged into contact with a surface. Sensing the contact force can aid in precisely positioning the electrode array when the contact force is critical (e.g. in an implanted retinal prosthesis), and can also provide information about the contact force over time.

The present invention further relates to a micromachined electrode array that comprises a semiconductor substrate (e.g. a silicon substrate), and a plurality of spaced-apart electrodes formed, at least in part, from the substrate. Each electrode is attached to the substrate by a plurality of springs to provide for movement of the electrode in a direction substantially normal to the substrate.

In some embodiments of the present invention, each electrode can comprise a base portion (i.e. an electrode seat) formed from the substrate, and an elongate metal portion (i.e. an electrode tip) attached to the base portion. Each electrode can be further overcoated with an electrically-insulating material except for an end of the metal portion distal to the base portion. In other embodiments of the present invention, each electrode can be formed from the substrate and can be overcoated with a metal or an electrically-conducting metal oxide. Generally, a majority of each electrode is further overcoated with an electrically-insulating material so that only a portion (e.g. 1–10 μm) of each electrode tip is exposed for electrically contacting a surface.

Each spring in the electrode array can comprise a folded spring; and the contact force for each electrode can be optionally made substantially the same when the electrode array is urged into contact with a curved surface such as that presented by the retina. In the electrode array, the substrate can include electrical wiring for providing a separate addressable electrical connection to each electrode. Additionally, the electrode array can include optional means for sensing a contact force for at least one of the plurality of electrodes when the electrode array is urged into contact with a surface (e.g. a neural surface such as the retina).

A flexible frame can also be provided attached to the substrate for positioning of the electrode array, or for attachment of the electrode array to a surface. Such a flexible frame is particularly useful when the electrode array forms a part of an implantable retinal prosthesis.

The present invention also relates to a micromachined electrode array that comprises a silicon substrate; a plurality of spaced-apart bulk-micromachined electrode seats formed from the substrate; a plurality of surface-micromachined springs formed in a polysilicon (i.e. polycrystalline silicon) layer deposited over the substrate, with each surface-micromachined spring being attached at one end thereof to the substrate, and at the other end thereof to one of the plurality of bulk-micromachined electrode seats; and an elongate electrode attached to or formed integrally with each bulk-micromachined electrode seat, with the electrode being oriented in a direction substantially normal to the substrate.

Each electrode can comprise a metal, or alternately can comprise a coating of a metal or an electrically-conductive metal oxide. Furthermore, each electrode can be overcoated with an electrically-insulating material. In some embodiments of the present invention, the electrode array can further include means for sensing a contact force for at least one electrode of the electrode array when the electrode array is urged into contact with a surface.

Each spring can comprise a folded spring. The springs attached to each electrode seat can also be optionally adapted to provide a spring constant which is inversely proportional to a displacement of the electrode seat whereon the springs are attached when the electrode array is urged into contact with a curved surface.

The electrode array can further comprise electrical wiring on the substrate for providing an electrical connection to each electrode in the electrode array. A flexible frame can also be attached to the substrate for handling of the electrode array, or for attaching the electrode array onto a surface to be electrically contacted thereby.

The present invention also relates to an electrode array for neural stimulation that comprises a silicon substrate, and a plurality of electrodes arranged in an array and protruding outward from a surface of the substrate, with each electrode comprising silicon and being flexibly attached to the substrate by a plurality of springs comprising polysilicon. Each electrode can have a width of generally 100 microns or less, and a length of generally one millimeter or less. Each electrode can also be overcoated with a metal (e.g. titanium, gold, platinum or iridium), or an electrically-conducting metal oxide (e.g. iridium oxide), or both. Additionally, a majority of each electrode can be overcoated with an electrically-insulating biocompatible material.

Each spring can comprise a folded spring. The spring constant of the springs can be tailored to provide a substantially-equal contact force for each electrode when the electrode array is urged into contact with a curved neural surface (e.g. an epiretinal surface) for electrical stimulation thereof. Electrical wiring can be formed on the substrate to provide an independently-addressable electrical connection to each electrode in the electrode array. Additionally, a flexible frame can be attached to the substrate for positioning of the electrode array to contact a neural surface (e.g. the epiretinal surface) for electrical stimulation thereof, or for attachment of the electrode array to the neural surface. Means can also be provided in the electrode array for sensing a contact force for one or more of the electrodes when the electrode array is urged into contact with a neural surface (e.g. an epiretinal surface).

Additional advantages and novel features of the invention will become apparent to those skilled in the art upon examination of the following detailed description thereof when considered in conjunction with the accompanying drawings. The advantages of the invention can be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several aspects of the present invention and, together with the description, serve to explain the principles of the invention. The drawings are only for the purpose of illustrating preferred embodiments of the invention and are not to be construed as limiting the invention. In the drawings.

DETAILED DESCRIPTION OF THE INVENTION

Figure 1:
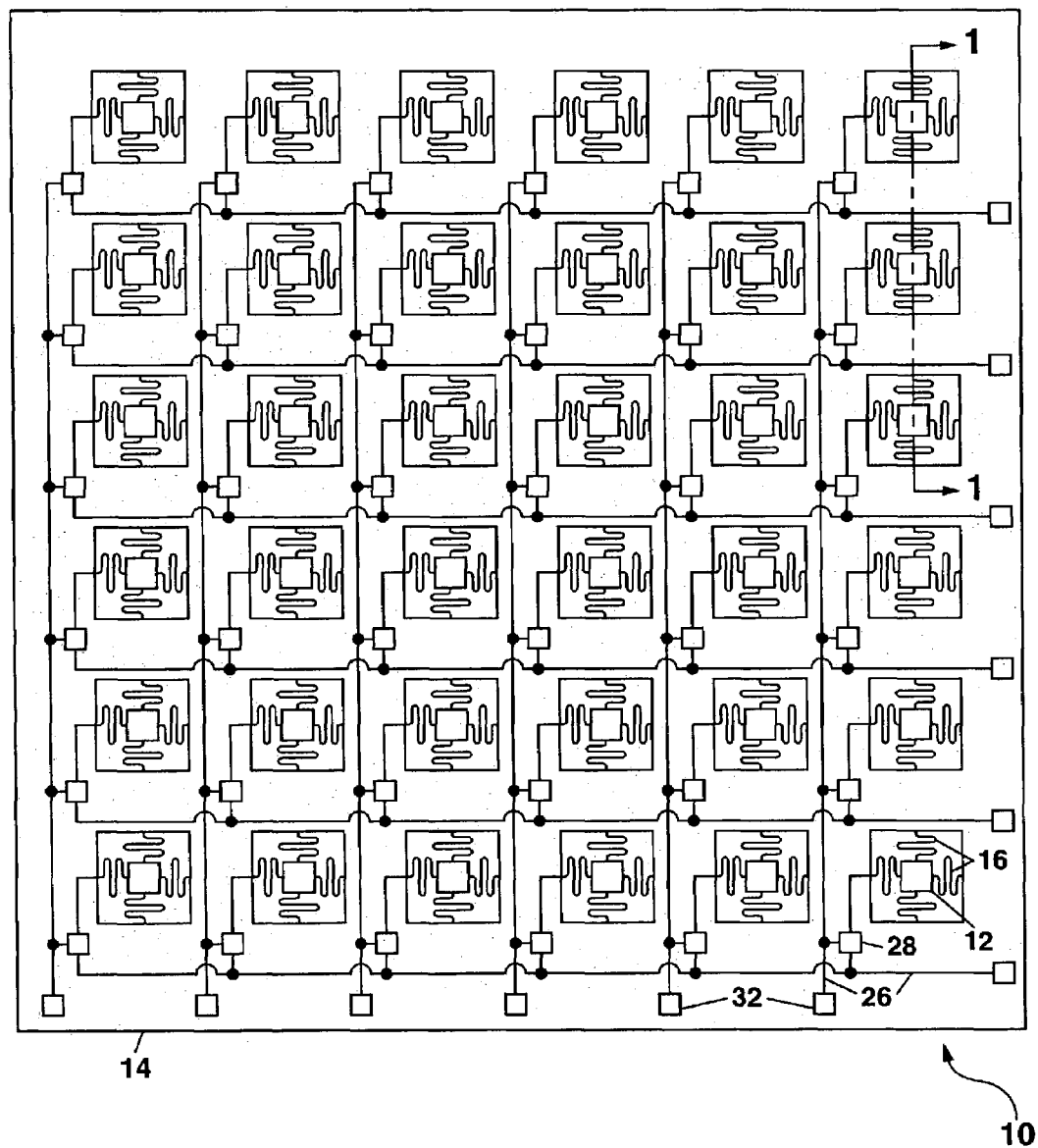
FIG. 1 shows a schematic plan view of an example of the electrode array of the present invention.

Referring to FIG. 1, there is shown a schematic plan view of an example of the electrode array 10 of the present invention. Although FIG. 1 illustrates a limited number of electrodes 12 in the array 10, those skilled in the art will understand that the electrode array 10 of the present invention can include up to hundreds, thousands or even millions of individual electrodes 12 depending upon the size and spacing of the individual electrodes 12 and the particular application for the device 10.

In FIG. 1, the electrode array 10 comprises a plurality of the electrodes 12 spaced apart from each other by a distance of, for example, 100–250 µm, with each electrode 12 being flexibly attached to a supporting substrate 14 by a plurality of springs 16. The springs 16 allow each electrode 12 to move independently in a direction which is substantially normal to a surface of the substrate 14 (i.e. perpendicular to the plane of FIG. 1). This is illustrated in FIGS. 2A and 2B which show schematic cross-section views along the section line 1—1 in FIG. 1.

The substrate 14 preferably comprises a semiconductor such as silicon which can be doped for electrical conductivity (e.g. n-type doped to about $10^{19}$ cm$^{-3}$ or more to provide a resistivity of, for example, 0.001–0.004 Ω-cm). The substrate 14 can initially be, for example, about 500 µm thick prior to fabrication of the electrodes 12 and can be thinned down to a final thickness of, for example, 100–300 µm, with the exact final thickness of the substrate 14 depending upon how the electrodes 12 are formed.

Figure 2A:
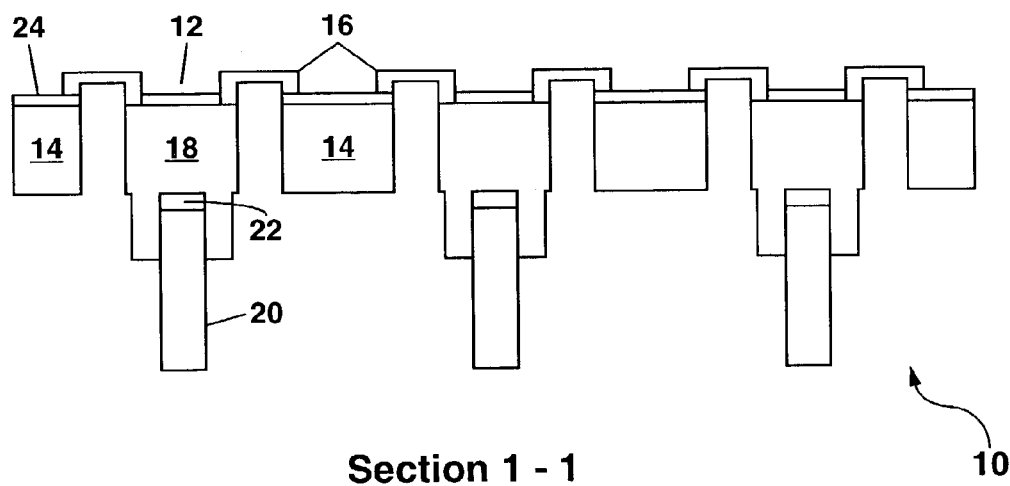
FIG. 2A shows a schematic cross-section view of a portion of the electrode array along the section line 1—1 in FIG. 1.
Figure 2B:
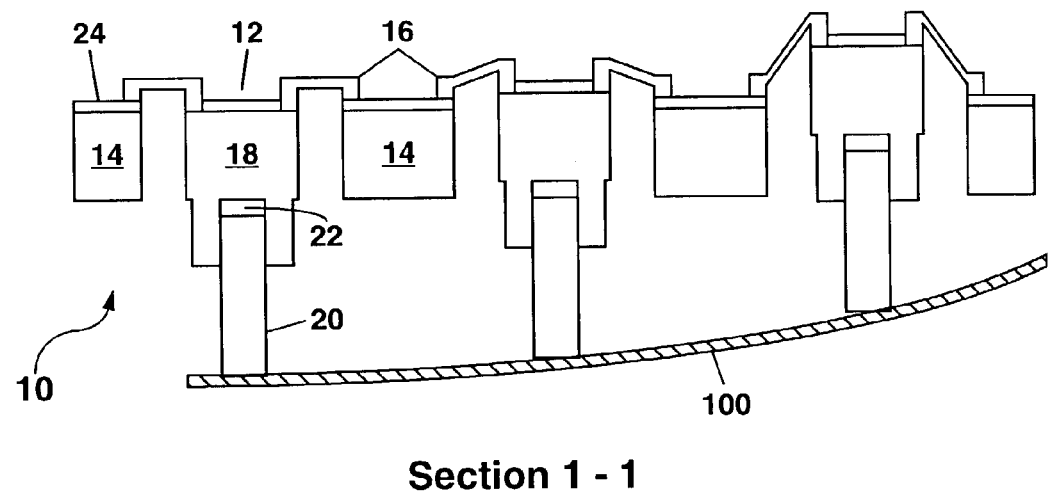
FIG. 2B shows the portion of the electrode array of FIG. 2A when urged into contact with a curved surface (e.g. an epiretinal surface) to illustrate the independent movement of each electrode in the array made possible by the springs which attach each electrode to the substrate.

FIG. 2A shows the electrode array 10 in an as-fabricated position with each electrode 12 comprising a bulk-micromachined electrode seat 18 formed from the substrate 14 and an elongate electrode tip 20 which is attached to the electrode seat 18. The electrode tips 20 can be either pressed into the electrode seats 18 or attached with an electrically-conductive adhesive 22 (e.g. an electrically-conductive epoxy). In other embodiments of the present invention as will be described in detail hereinafter, the electrode tips 20 can be formed integrally with the electrode seats 18 by electroplating, or by etching the electrode seats 18 and the tips 20 out of the semiconductor substrate 14, or a combination thereof.

In FIG. 2A, each electrode 12 is flexibly attached to the surrounding substrate 14 by a plurality of springs 16 which are generally formed from polysilicon (i.e. polycrystalline silicon) or metal and which can be electrically insulated from the substrate 14 by an electrically-insulating layer 24 which generally comprises silicon nitride. One or more of the springs 16, which are preferably formed from doped polysilicon for electrical conductivity (e.g. n-type doped with phosphorous to about $10^{19}$ cm$^{-3}$ or more), can be used to electrically connect each electrode 12 to addressing circuitry 26 (i.e. wiring) located on the substrate 14. The addressing circuitry 26 can include a plurality of switching transistors 28 formed in the silicon substrate 14 to allow row and column addressing of the individual electrodes 12 in the array 10. A plurality of bond pads (32) can be provided around the periphery of the substrate 14 to allow the addressing circuitry 26 to be connected to other electronic circuitry (e.g. for providing addressing information to the switching transistors 28, for providing electrical signals to the electrodes 12 for neural stimulation, for sensing electrical signals from neural tissue using the electrodes 12, etc.). Alternately, the electronic circuitry can be located on a separate substrate which is attached to the electrode array 10 (see FIG. 7) with the electrical connections to the addressing circuitry 26 being made through a plurality of electrical interconnections between the substrates.

Each electrode 12 is flexibly attached to the substrate 14 by a plurality of springs 16 to allow an extended range of displacement of the electrode 12 of up to about 500 µm depending upon a particular application for the electrode array 10. This extended range of movement is made possible by the use of springs 16 which have an overall length that can be in the range of 0.2–1 millimeter and lateral dimensions in the range of 1–5 µm. To save space, the springs 16 can be curved around the electrodes 12 (see FIGS. 10C and 10D) or else folded. The term "folded" as used herein refers to a spring 16 that has a shape which folds back on itself one or more times (e.g. a serpentine shape as shown in FIGS. 1 and 10B). The term "folded" as used herein also refers to a spring 16 that includes one or more 90° bends (see FIG. 10A).

In FIG. 2B, operation of the electrode array 10 is schematically illustrated for contacting a curved surface 100. Here, the springs 16 allow the electrodes 12 to move independently and thereby conform to the surface 100 as the electrode array 10 is urged into contact therewith. An advantage of the electrode array 10 of the present invention is that each electrode 12 is moveable independent of the other electrodes 12 so that the electrode array 10 can be used to make contact with surfaces of arbitrary shape. In particular, the electrode array 10 can be used to contact a neural surface such as the retina inside an eye without a need to bend the substrate 14 or to shape the electrodes 12 to fit a curved surface presented by the inside of the retina (although shaping of the electrodes 12 can be performed for certain embodiments of the electrode array 10 as will be described hereinafter).

Another advantage of the electrode array 10 of the present invention is that a spring constant, k, for each spring 16 in the electrode array 10 can be tailored to provide a substantially equal contact force, F, when the electrode array 10 is urged into contact with a surface of a known shape (e.g. a curved surface such as an epiretinal surface). This can be done, for example, by designing a photomask pattern that will be used to form the springs 16 by surface micromachining to provide a predetermined width or length for each spring 16 connected to a particular electrode 12 so that the spring constant, k, for each spring 16 will be inversely related to an expected displacement, x, for that electrode 12. Then the force, F=−nkx, provided by each electrode 12 due to a stretching of the number, n, of the springs 16 attached to that electrode 12 will be substantially the same. The electrodes 12 can each provide a contact force that is on the order of a few microNewtons up to tens of microNewtons depending upon a particular application of the device 10.

Control over the contact force of each electrode 12 is particularly important when the electrode array 10 is to be used as part of a retinal prosthesis since nerve cells in the retina can be damaged by excessive pressure. The retina's sensitivity to pressure can be inferred from the onset of glaucoma in human eyes which can occur for chronic excess fluid pressures of about 10 mm of mercury. Thus, when used as part of a retinal implant for the artificial stimulation of neural cells (e.g. ganglion cells), the electrode array 10 should preferably provide a controllable and well-defined contact pressure that is substantially the same for all electrodes 12 when the electrode array 10 is urged into contact with the curved epiretinal surface. This can be done, for example, by decreasing the spring constant, k, with distance radially outward from the center of the electrode array 10, with the spring constant, k, for each spring 16 attached to an electrode 12 located at a given radius being inversely proportional to the expected displacement, x, of that electrode 12.

Figure 3A:
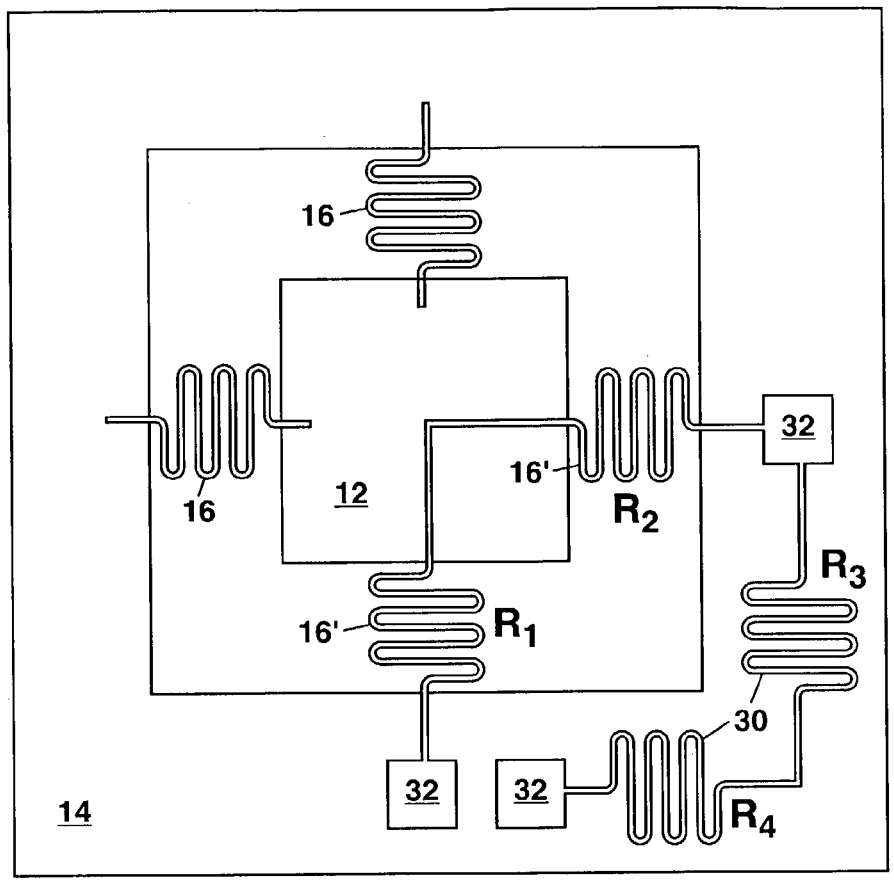
FIG. 3A shows a schematic plan view of an electrode of the array of FIG. 1 that has been configured to provide for piezoresistive sensing of a contact force of that electrode.
Figure 3B:
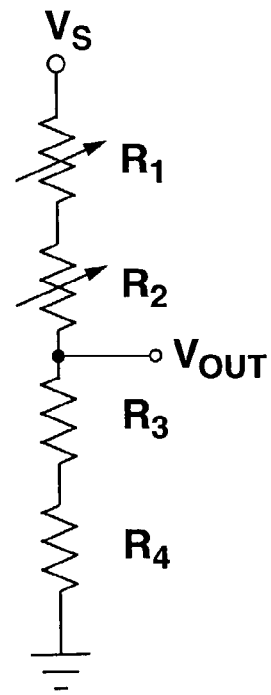
FIG. 3B shows a schematic diagram of an equivalent electrical circuit for the piezoresistive sensing of the contact force using the electrode in FIG. 3A.

Yet another advantage of the electrode array 10 of the present invention is that the contact force for one or more of the electrodes 12 can be sensed while the electrode array is in contact with a surface of arbitrary shape. This can be done by utilizing the piezoresistivity of the polysilicon used to form the springs 16 which provides a change in resistance for each spring 16 as a function of a deflection of that spring 16. FIGS. 3A and 3B illustrate this method for providing an in situ or in vivo sensing of the contact force of one or more electrodes 12 of the array 10.

In FIG. 3A, a pair of the springs 16' are electrically insulated from the electrode 12 by an electrically-insulating layer of silicon nitride 24 disposed between the springs 16' and the electrode 12; and these springs 16' are used to form variable resistors $R_1$ and $R_2$, with the resistance of each resistor $R_1$ and $R_2$ varying in proportion to the displacement of the electrode 12 and springs 16' according to the piezoelectric effect within one or more layers of polysilicon used to form the springs 16' and an initial resistance of springs' without any displacement thereof. One or more of the remaining springs 16 in FIG. 3 can be electrically connected to the electrode 12 through openings formed in the silicon nitride layer 24 thereby forming a current path between the electrode 12 and the addressing circuitry 26 (see FIG. 1).

In FIG. 3A, a pair of fixed resistors 30 denoted as $R_3$ and $R_4$ can be formed over the silicon nitride layer 24 on the substrate 14 and electrically connected in series with the variable resistors $R_1$ and $R_2$. The resistors $R_1$ through $R_4$ can be further connected to bond pads 32 as shown in FIG. 3A or alternately to electrical wiring formed on the substrate 14, with the resistors $R_1$ through $R_4$ preferably being arranged to form a Half-Wheatstone-Bridge circuit as shown in FIG. 3B. The Half-Wheatstone-Bridge circuit, when connected to a voltage source, $V_S$, provides an output voltage, $V_{OUT}$, that is responsive to changes in the displacement of the electrode 12 and springs 16' thereby allowing the displacement and contact force to be determined from the output voltage, $V_{OUT}$. The resistors $R_1$ through $R_4$ can all have substantially the same initial resistance when the springs 16' are at rest in an undeflected position. A calibration of the Half-Wheatstone-Bridge circuit can be performed, for example, by measuring the output voltage, $V_{OUT}$, with the springs 16' in the undeflected position and then providing a known displacement or contact force on the electrode 12 and measuring a change in the output voltage, $V_{OUT}$, from that in the undeflected position.

The ability provided by the electrode array 10 in certain embodiments of the present invention to sense the contact force for one or more electrodes 12 is particularly useful for implanted neural prosthesis since this can provide a way of monitoring the pressure exerted by the individual electrodes 12 on neural tissue which has not heretofore been possible. Such monitoring can be performed, for example, during implantation of a retinal prosthesis to allow forces exerted on the retina to be sensed during implantation and to be monitored periodically or continuously throughout the use of the retinal prosthesis.

Figure 4A:
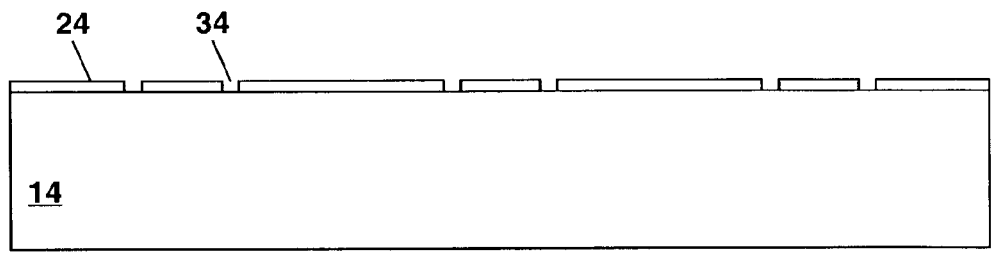
FIGS. 4A–4R show schematic cross-section views along the section line 1—1 in FIG. 1 to illustrate fabrication of a first embodiment of the present invention as shown in FIGS. 1 and 2A–2B.
Figure 4B:
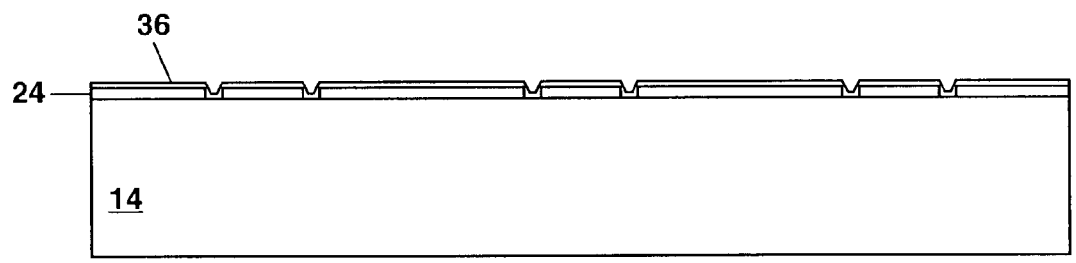
Figure 4C:
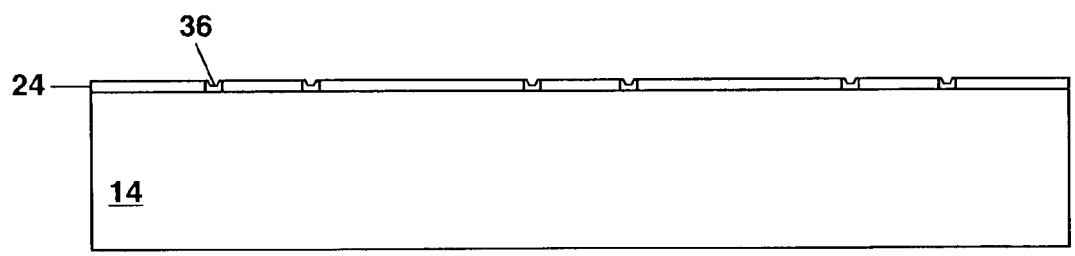
Figure 4D:
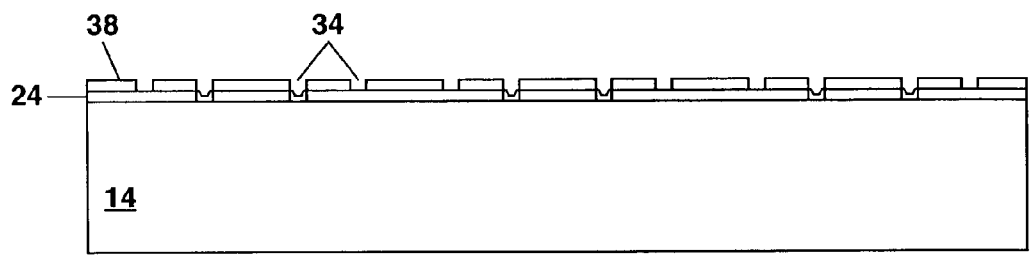
Figure 4E:
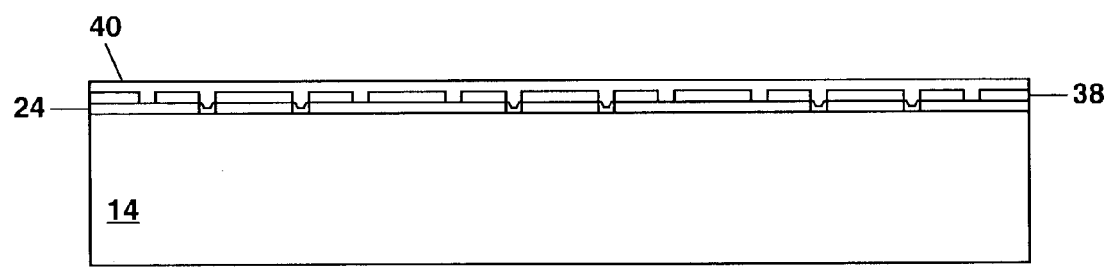
Figure 4F:
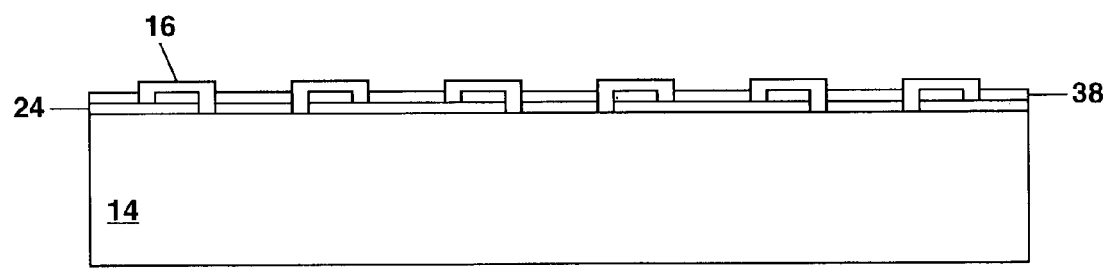
Figure 4G:
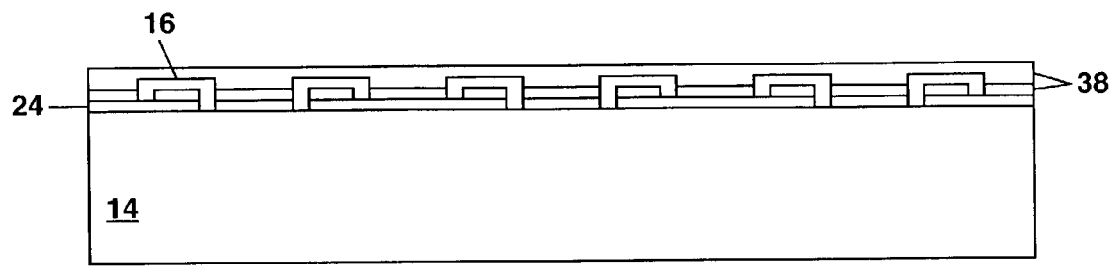
Figure 4H:
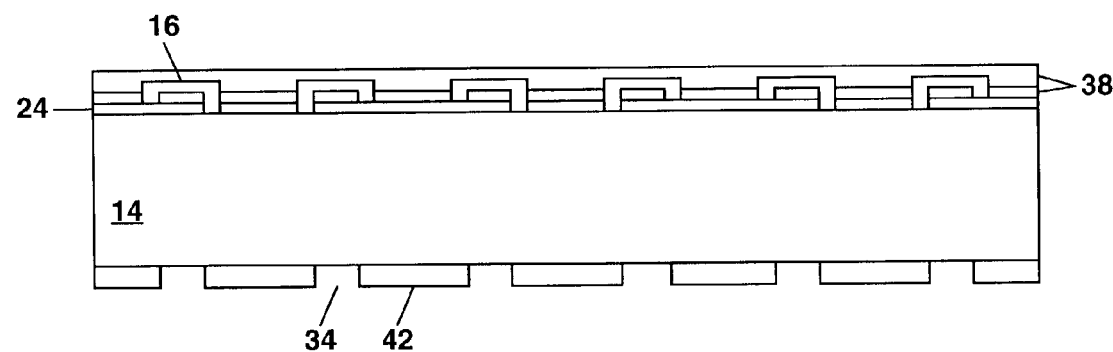
Figure 4I:
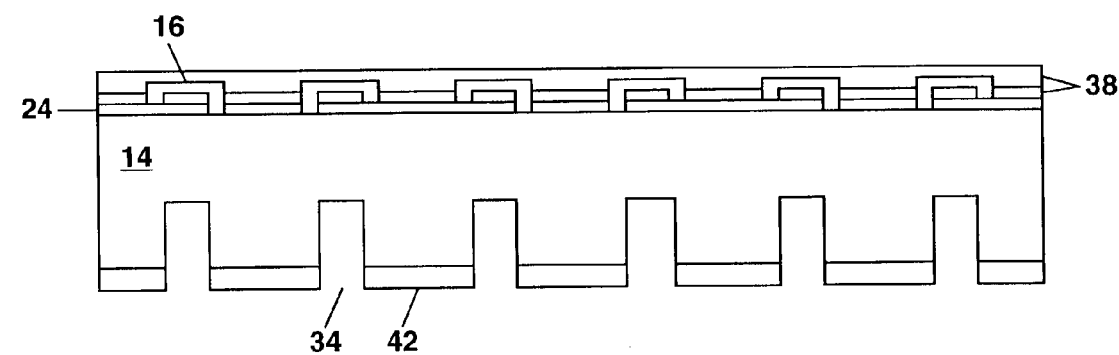
Figure 4J:
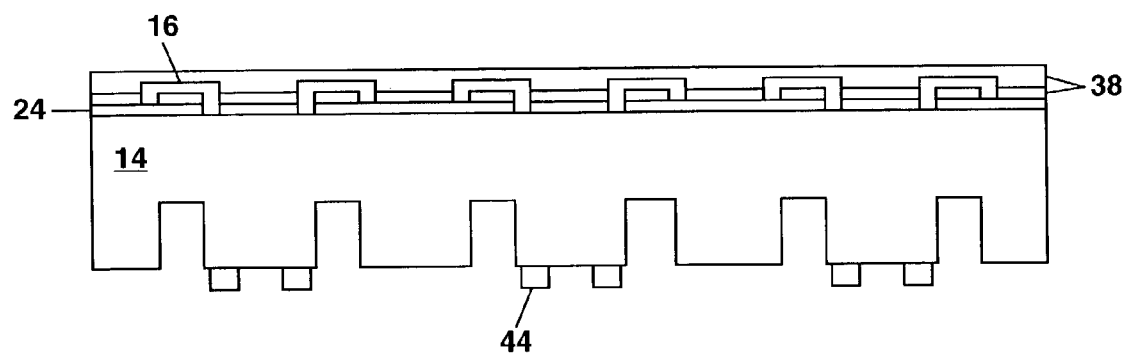
Figure 4K:
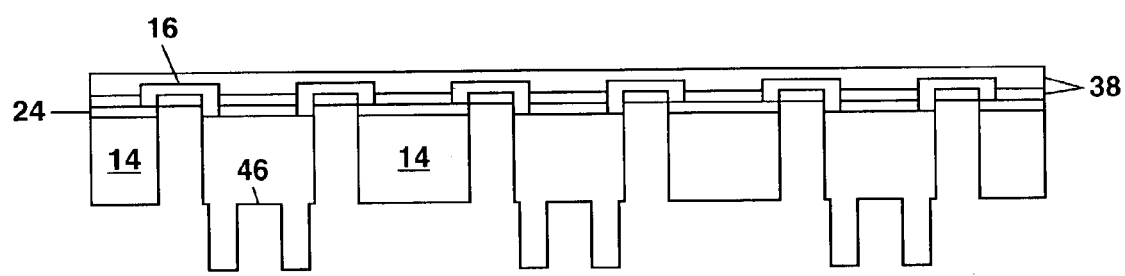
Figure 4L:
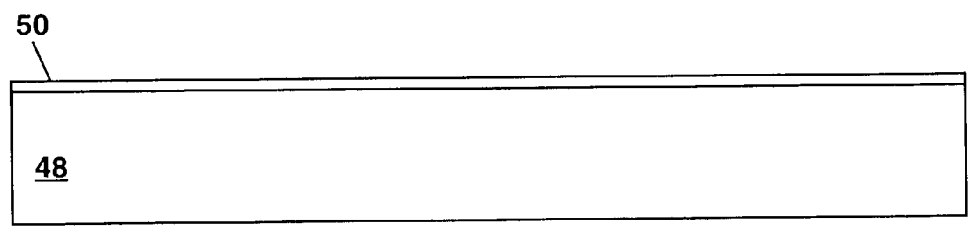
Figure 4M:
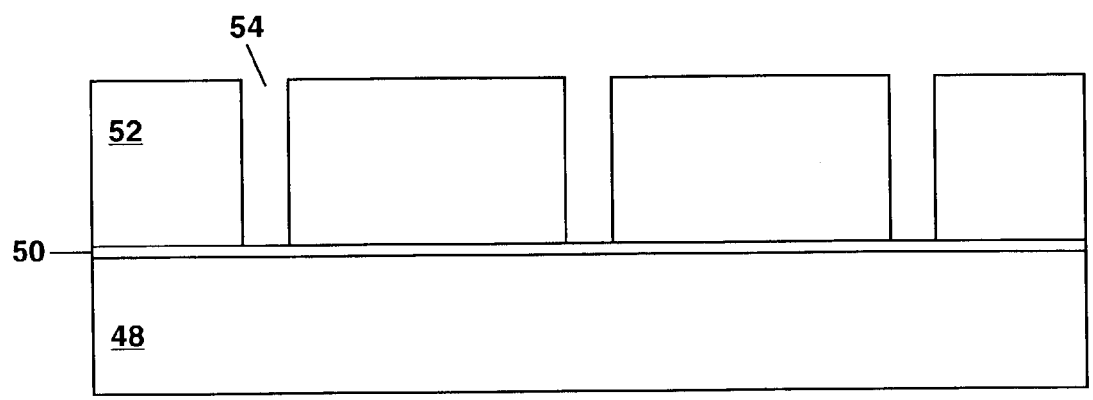
Figure 4N:
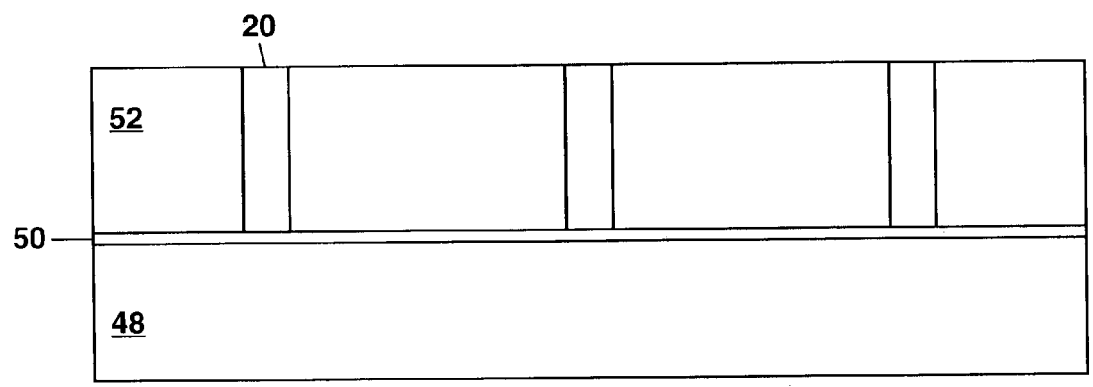
Figure 4O:
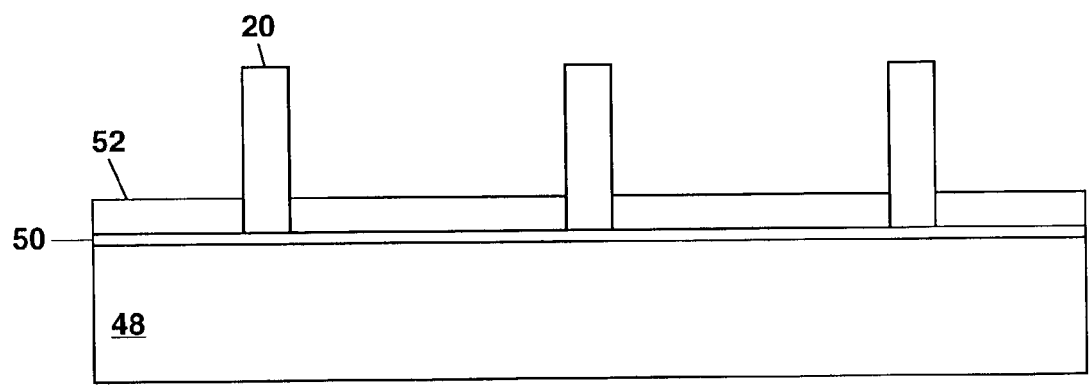
Figure 4P:
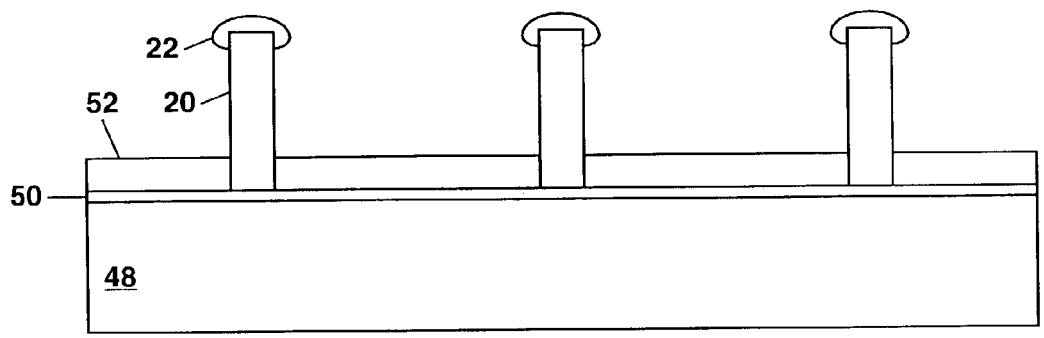
Figure 4Q:
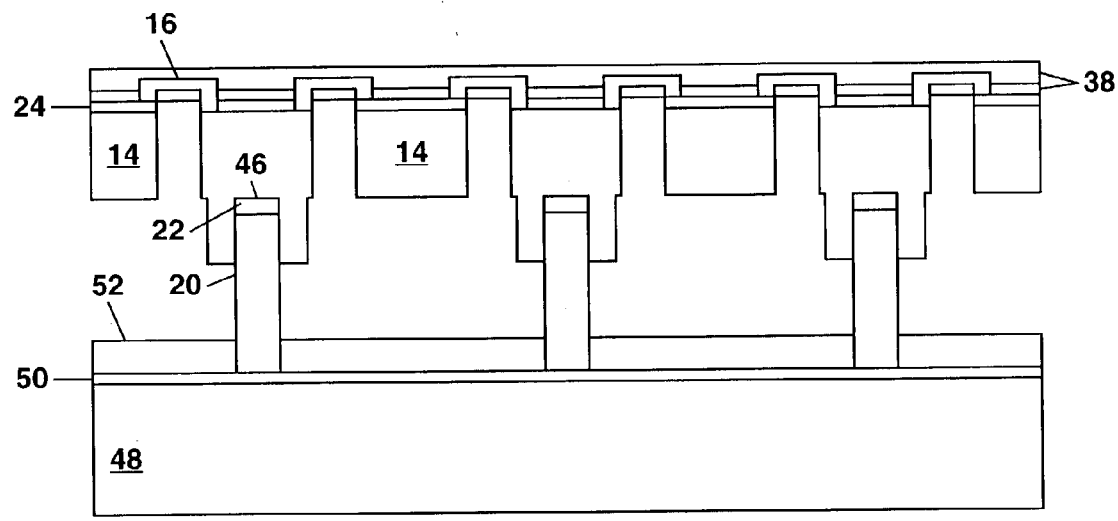
Figure 4R:
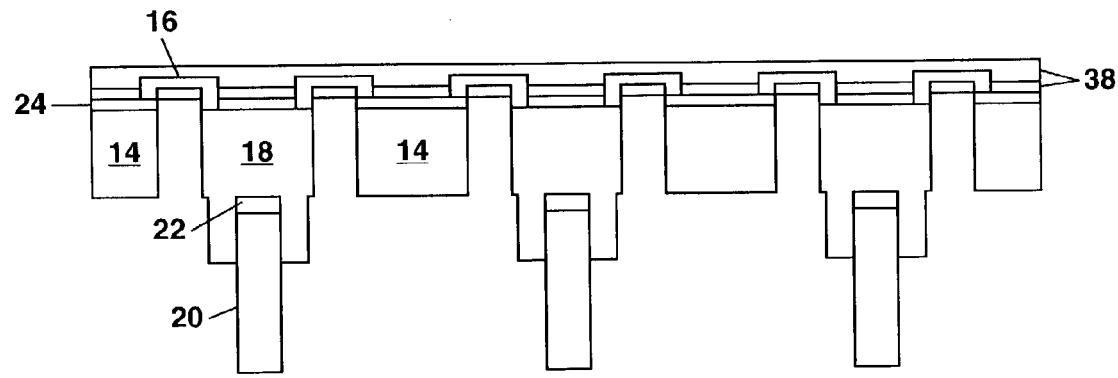

FIGS. 4A–4R show schematic cross-section views along the section line 1—1 in FIG. 1 to illustrate a process for fabricating a first embodiment of the electrode array 10 of the present invention using surface and bulk micromachining as known to the art. Surface and bulk micromachining processes are based on conventional IC processing steps, including repeated steps for material deposition, photolithography, masking, etching, mask stripping, and cleaning. Only the essential steps for fabricating the electrode array 10 of the present invention will be described in detail herein.

In FIG. 4A, a heavily-doped ($\geq 10^{19}$ cm$^{-3}$) n-type silicon substrate 14 is initially prepared for fabrication of the electrode array 10 by blanketing the substrate 14 with a layer of a thermal oxide (not shown) which can be 630 nanometers thick and formed by a conventional wet oxidation process at an elevated temperature (e.g 1050° C. for about 1.5 hours). A low-stress layer 24 of silicon nitride (e.g. 800 nanometers thick) can then be blanket deposited over the substrate 14 using low-pressure chemical vapor deposition (LPCVD) at about 850° C. The thermal oxide layer and the silicon nitride layer 24 provide electrical isolation from the substrate 14 for certain elements of the electrode array 10 (e.g. the springs 16, the addressing circuitry 26 and the fixed resistors 30). A plurality of openings 34 can be formed through the thermal oxide layer and the silicon nitride layer 24 in preparation for electrically connecting the springs 16 to the electrode seats 18.

In FIG. 4B, a first polysilicon layer 36 (denoted Poly-0) can be blanket deposited over the substrate 14 by LPCVD at a temperature of about 580° C. and with a layer thickness of, for example, 300 nanometers. The Poly-0 layer 36 can be used to form part of the addressing circuitry 26 together with a subsequently-deposited second polysilicon layer 40 (denoted Poly-1) described hereinafter with reference to FIGS. 4E and 4F. Additionally, the Poly-0 layer 36 is used to connect the springs 16 to the electrode seats 18 which will be formed from the substrate 14 in later process steps. Phosphorous doping can be used to make the Poly-0 and Poly-1 layers 36 and 40 electrically conductive.

In FIG. 4C, the Poly-0 layer 36 is patterned to form a first layer of the addressing circuitry 26 (see FIG. 1) on the silicon nitride layer 24, and to leave portions of the Poly-0 layer 36 on the substrate 14 at the locations of the openings 34 through the silicon nitride layer 24. The term "patterning" as used herein refers to a sequence of well-known semiconductor integrated circuit processing steps including applying a photoresist to the substrate 14, prebaking the photoresist, aligning the substrate 14 with a photomask, exposing the photoresist through the photomask, developing the photoresist, baking the photoresist, etching away the surfaces not protected by the photoresist, and stripping the protected areas of the photoresist so that further processing can take place. The term "patterning" can further include the formation of a hard mask (e.g. comprising about 500 nanometers of a silicate glass deposited from the decomposition of tetraethylortho silicate, also termed TEOS, by low-pressure chemical vapor deposition at about 750° C. and densified by a high temperature processing) overlying a polysilicon, metal or sacrificial material layer in preparation for defining features into the layer by etching.

In FIG. 4D, a first layer of a sacrificial material 38 can be blanket deposited over the substrate 14 by LPCVD and patterned to form openings 34 at the locations of each end of the springs 16. The sacrificial material 38, which can be about 2 μm thick, can comprise silicon dioxide ($SiO_2$) or a silicate glass (e.g. TEOS which is deposited from the decomposition of tetraethylortho silicate by low-pressure chemical vapor deposition at about 750° C. followed by densification at a higher temperature).

In FIG. 4E, the second polysilicon layer 40 (Poly-1) is blanket deposited over the substrate 14 by LPCVD, filling in the openings 34 for use in building up the springs 16 and for providing a second layer of the addressing circuitry 26. In FIG. 4F, the Poly-1 layer is patterned using reactive ion etching to form the springs 16 and the second layer of the addressing circuitry 26. The Poly-1 layer 40 can be 1–2 μm thick. If needed, additional layers of polysilicon (not shown) can be deposited over the Poly-1 layer 40 and laminated thereto to build up the springs 16 to a greater thickness.

In other embodiments of the present invention, a metal (e.g. aluminum or an aluminum alloy) can be substituted for the polysilicon in the layers 36 and 40 to form the addressing circuitry 26 and the springs 16.

In FIG. 4G, once the springs 16 have been formed, they are encapsulated in another layer of the sacrificial material 38. A thermal annealing step can then be provided to anneal out any residual stress in the polysilicon layers 24 and 40. This annealing step can be performed at an elevated temperature of about 1100° C. for several hours (e.g. 3 hours).

In FIG. 4H, a patterned etch mask 42 can be formed on a backside of the substrate 14 in preparation for etching through the substrate 14 to form the electrode seats 18. The etch mask 42 includes a plurality of shaped openings 34 at locations where the substrate 14 will be etched away. The etch mask 42 can comprise a hard etch mask as described previously and can be formed in part from the layers of silicon nitride, polysilicon and the sacrificial material 38 which are also generally deposited on the backside of the substrate 14 when LPCVD is used, although these layers have been omitted from FIGS. 4A–4G for clarity.

In FIG. 4I, the substrate 14 can be etched from the backside to remove portions of the substrate 14 that are exposed by the openings 34 through the etch mask 42 and thereby begin to form the electrode seats 18. The electrode seats 18 can have lateral dimensions of, for example, 100 μm. The etching process used to remove material from the substrate 14 can comprise a deep anisotropic plasma etching process which has been termed a Bosch etch process. The Bosch etch process is disclosed in U.S. Pat. No. 5,501,893 to Laermer, which is incorporated herein by reference. This Bosch etch process combines multiple anisotropic etching steps with steps for simultaneously depositing an isotropic polymer/inhibitor to minimize lateral etching thereby allowing openings to be etched through the substrate 14 to a depth of up to the thickness of the substrate 14 while retaining substantially uniform lateral dimensions (i.e. straight sidewalls) for the etched openings.

In FIG. 4J, the etch mask 42 can be re-patterned or replaced by another etch mask 44 which is used for a second Bosch etch step which can be terminated upon reaching the silicon nitride layer 24, or which can be used to etch through both the substrate 14 and the silicon nitride layer 24 as shown in FIG. 4K. The second Bosch etch step forms the electrode seats 18 and separates the electrode seats 18 from the remaining substrate 14. Additionally, the second Bosch etch step can be used to form a receptacle 46 in each electrode seat 18 wherein an electrode tip 20 can later be inserted and attached. Each receptacle 46 can be, for example, 10–100 μm in diameter depending upon the size of the electrode tips 20 to be used in the array 10. Although the receptacles 46 are shown in FIG. 4K as having straight sidewalls 46, the receptacles 46 can be optionally be formed with sloping sidewalls 46 (i.e. tapered inward with increasing depth of etching). Tapering of the receptacles 46 can be performed, for example, using a conventional reactive ion etching step.

The electrode tips 20 can, in turn, be sized to fit a particular type of neuron which is to be stimulated by or sensed with the electrode array 10. As an example, ganglion cells in the retina are typically about 10–20 μm in diameter, so that each electrode tip 20 can be about this size if single ganglion cells are to be stimulated with the electrode array 10 in a retinal prosthesis, and the diameter of the electrode tips 20 can be scaled upward from this size when multiple ganglion cells are to be stimulated by each electrode tip 20.

In FIG. 4K, after the second Bosch etch step is completed, the etch mask 44 can be removed. As shown in FIG. 4K, the remaining substrate 14, which is not covered by the etch mask 44, can be thinned (e.g. down to 100–300 μm thickness) by the second Bosch etch step. This allows the electrode seats 18 to protrude outward from the backside of the substrate 14. Although the silicon nitride layer 24 is shown removed underneath the springs 16 in FIG. 4K after the second Bosch etch step, the silicon nitride layer 24 can also be left in place after the second Bosch etch step is completed and removed in a later step (e.g. by etching from a topside of the substrate 14). Additionally, the silicon nitride layer 24 can be optionally patterned in later steps to form a stop (not shown) underneath each spring 16 to limit a downward movement of the spring 16 (e.g. when the spring 16 is loaded by the added weight of the electrode tips 20).

In FIG. 4L, formation of the electrode tips 20 is commenced in another series of processing steps by providing a sacrificial substrate 48 whereon the electrode tips 20 can be formed by electroplating. A release layer 50 can be formed over a surface of the sacrificial substrate 48, with the release layer 50 being used to later separate the electrode tips 20 which will be formed by electroplating from the sacrificial substrate 48. The sacrificial substrate 48 can comprise, for example, silicon, glass, fused silica, alumina, sapphire or metal. The material used to form the sacrificial substrate 48 is generally not critical since it serves only as a support whereon the electrode tips 20 can be electroplated.

The release layer 50 can comprise, for example, copper or polymethyl methacrylate (PMMA). An electroplating seed layer (not shown) can be provided over the release layer for use in electroplating a metal such as platinum, iridium, titanium or gold or a combination thereof for forming the electrode tips 20. The seed layer can also be used to make an electrical connection for electroplating, especially when an electrically-insulating release layer such as PMMA is used. Those skilled in the art will understand that, while the above-cited metals are preferred for reasons of biocompatibility when the electrode array 10 is to be used for neural stimulation, other metals and electrically-conductive metal oxides can be used to form the electrode tips 20 for applications of the electrode array 10 other than neural sensing.

The process steps described herein for forming the electrode tips 20 in FIGS. 4L–4N are based on LIGA (an acronym based on the first letters for the German words for lithography and electroplating) which is well-known in the art. LIGA utilizes deep x-ray lithography (e.g. using synchrotron radiation) to form an electroplating mask 52 from a sheet resist material (e.g. PMMA) which can be patterned with micron-sized features and which can have a large aspect ratio as shown in FIG. 4M. The electroplating mask 52, which includes a plurality of shaped openings 54 at the locations wherein the electrode tips 20 are to be formed, can then be used to electroplate the electrode tips 20 on the release layer 50 as shown in FIG. 4N. The electrode tips 20 are formed as an array with a spacing corresponding to that of the receptacles 46 formed in the electrode seats 18 in FIG. 4K and with a length, for example, of up to 500 µm so that an overall length of the electrodes 12 is generally about one millimeter or less. The electrode tips 20 are generally sized to be slightly smaller in width than the receptacles 46 so that the electrode tips 20 can later be inserted therein all at once and attached to the electrode seats 18 by an adhesive or a friction fit.

In FIG. 4O, the electroplating mask 52 can be removed in part (e.g. by solvent dissolution or plasma etching) to expose the ends of the electrode tips 20 in preparation for inserting the electrode tips 20 into the electrode seats 18.

In FIG. 4P, an electrically-conductive adhesive 22 (e.g. an electrically-conductive epoxy) can be applied to the exposed ends of the electrode tips 20 immediately prior to mating the electrode tips 20 with the electrode seats 18 as shown in FIG. 4Q. In other embodiments of the present invention, the electrode tips 20 can be inserted into the electrode seats 18 and held in place by a friction fit. This can be done, for example, by heating the electrode seats 18 and cooling the electrode tips 20 and then mating the two together. Alternately, the electrode tips 20 can be urged into the electrode seats 18 with a backing (e.g. PMMA or a silicone polymer such as poly-dimethylsiloxane, also termed PDMS) being provided on a topside of the substrate 14 for protection and added stiffness. The electrode tips 20 can be rounded or pointed (e.g. by electropolishing or etching), if needed, to facilitate mating of the electrode tips 20 to the electrode seats 18.

In FIG. 4R, once the electrode tips 20 have been inserted into the electrode seats 18 and the adhesive 22 has cured, the electrode tips 20 can be separated from the sacrificial substrate 48 by selectively etching away the release layer 50 (e.g. using an acid for a copper release layer 50) or by dissolving the release layer 50 in a solvent such as acetone (e.g for a PMMA release layer 50). During this step, the electroplating seed layer can also be removed from the electrode tips 20.

If needed, an additional layer of metal or a metal oxide (e.g. iridium oxide) can be deposited over the ends of the electrode tips 20 for improved electrical conductivity or for compatibility when interfacing with a particular type of neural tissue or other surface with which the electrode array 10 is to be used. Such an additional layer of metal or metal oxide (not shown in FIG. 4R) can be deposited over the electrode tips 20 by a conventional deposition process (e.g. sputtering or evaporation), or by electroplating. An iridium oxide surface can be formed on electrode tips 20 comprising iridium by a thermal oxidation step whereby the iridium on exposed surfaces of the electrode tips 20 is converted to iridium oxide at an elevated temperature.

The layers of the sacrificial material 38 in FIG. 4R can then be removed with a selective etchant comprising hydrofluoric acid (HF) to release the individual electrodes 12 for movement and to complete the fabrication of the electrode array 10. This can be done by immersing the electrode array 10 in an HF solution for a time period ranging from several minutes up to several hours.

The formation of a plurality of switching transistors 28 on the substrate 14 for addressing the individual electrodes 12 in the array 10 can be performed during the fabrication of the other elements of the electrode array 10 described with reference to FIGS. 4A–4C. The transistors 28 can be formed in the substrate 14 by a series of standard integrated circuit (IC) processing steps including ion implantation or dopant diffusion to form drain and source regions for the transistors 28 which are preferably field-effect transistors (FETs). The Poly-0 layer 36 can be used to form a gate between the source and drain of each transistor, with the thermal oxide being used as a gate oxide to separate the gate from a channel region formed in the substrate 14 between the drain and source regions. The Poly-0 layer 36 can also be used for electrical interconnections to the gate and the drain and source regions. Electrical isolation of each transistor 28 from the substrate 14 can be provided by forming the drain, source and channel regions with a dopant type which is opposite the doping type used for the substrate 14 (i.e. by forming reverse-biased diode junctions between the drain, source and channel regions and the substrate 14), or alternately by using a silicon-on-insulator substrate 14 with the electrical isolation being provided by an oxide layer (i.e. $SiO_2$) underlying each transistor 28 and an isolation trench formed about each transistor 28 and filled with either silicon nitride (i.e. the silicon nitride layer 24) or with the sacrificial material 38.

Although the materials (e.g. silicon, silicon dioxide, silicon nitride, platinum, iridium, gold, titanium and/or iridium oxide) used to fabricate the electrode array 10 are generally biocompatible, in certain embodiments of the present invention used for neural stimulation (e.g. for use in a retinal prosthesis), a thin layer (e.g. up to about 0.1 µm) of an electrically-insulating biocompatible material such as parylene (i.e. a para-xylene polymer), silicon dioxide or silicon nitride can be conformally deposited over all exposed surfaces of the electrode array 10 and then selectively removed at the ends of electrode tips 20 (e.g. from the end and backwards for a distance of 1–10 µm). This conformal deposition can be performed by LPCVD in the case of silicon dioxide or silicon nitride. The selective removal of the electrically-insulating biocompatible material at the ends of the electrode tips 20 can be performed using laser ablation, solvent dissolution, or etching depending on the particular biocompatible material used.

Parylene, which is produced by the condensation and polymerization of a gaseous monomer, para-xylylene, can be conformally deposited at room temperature using a vapor deposition polymerization (VDP) process in commercial VDP apparatus. The VDP process is disclosed by Gorham in U.S. Pat. No. 3,342,754, which is incorporated herein by reference. In the VDP process, a parylene dimer (e.g. di-para-xylylene) is heated in the VDP apparatus to about 150° C. resulting in its conversion to a gaseous dimer. This causes the gas pressure in a vaporization zone wherein the parylene dimer is heated to rise, forcing the dimeric gas downstream into a pyrolysis zone where it is then heated further to about 650° C., splitting the dimer molecules into highly reactive monomer molecules (e.g. para-xylylene). The monomer molecules continue to respond to pressure, flowing into a room-temperature deposition chamber of the VDP apparatus where the monomer molecules disperse and grow as a clear linear-polymer film on all surfaces to which the monomer molecules are exposed. The thickness of the resultant parylene coating can be controlled by the volume of the parylene dimer that is vaporized and by the dwell time in the deposition chamber. Since the parylene deposition process is gaseous, the coating thickness is uniform and conformal, covering all exposed surfaces of the electrode array 10 and any other elements (e.g. electronic circuitry, wiring, etc.) attached thereto, without any associated cure stress.

In other embodiments of the present invention, the electrode tips 20 can be formed directly on the electrode seats 18 as described hereinafter with reference to FIGS. 5A–5C and FIGS. 6A–6F.

Figure 5A:
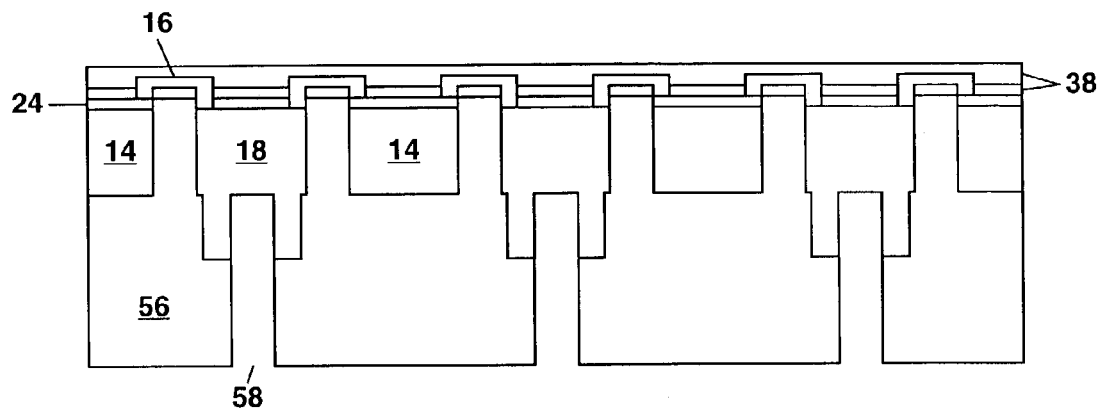
FIGS. 5A–5C illustrate the fabrication of a second embodiment of the present invention beginning after the process step described with reference to FIG. 4K.
Figure 5B:
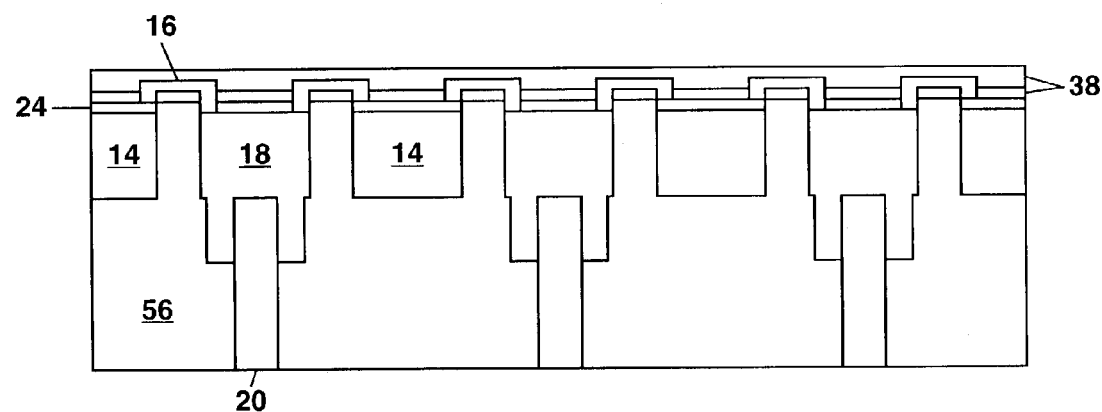
Figure 5C:
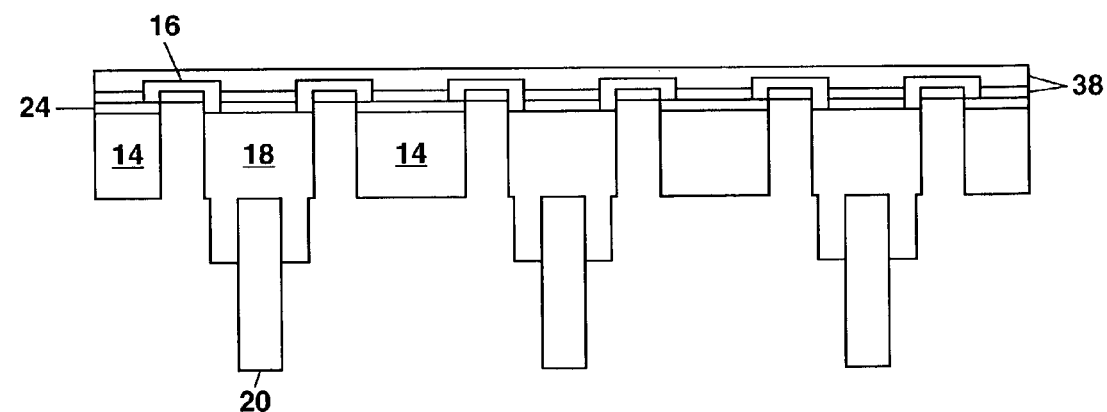

In FIGS. 5A–5C, the electrode tips 20 can be electroplated directly onto the electrode seats 18. This can be done, for example, by providing a thick patterned mask 56 over the backside of the substrate 14 as shown in FIG. 5A after the process step described with reference to FIG. 4K, with openings 58 defined photolithographically or by deep x-ray lithography at the locations of each electrode seat 18 wherein the electrode tips 20 are to be formed. The mask 56, which can have a thickness that is substantially equal to the length of the electrode tips 20 to be formed, can comprise one or more layers of a photoresist, or alternately a polymer material such as PMMA or PDMS. In some embodiments of the present invention, the mask 56 can be shaped (e.g. by reflowing the photoresist, by molding the PMMA or PDMS, etc.) to form the electrode tips 20 with different lengths across the electrode array 10 (e.g. to form the electrode tips 20 with a convex shape). This can be advantageous for equalizing or limiting the displacement of the electrode tips 20 when the electrode array 10 is to be urged into contact with a curved surface, and thereby equalizing a contact force of the electrodes 12 when the springs 16 all have substantially the same spring constant.

Although a plurality of receptacles 46 are shown in FIG. 4K, the formation of receptacles 46 is optional when the electrode tips 20 are to be electroplated directly onto the electrode seats 18. Omitting formation of the receptacles 46 and etching the electrode seats 18 to the same thickness as the remainder of the substrate 14 can facilitate the formation of the mask 56 especially when a sheet resist material such as PMMA is used to allow patterning of the mask 56 by deep x-ray lithography, with the sheet PMMA material being attached to the substrate 14 with an adhesive.

Once the patterned mask 56 has been provided over the backside of the substrate 14 as shown in FIG. 5A and the openings 58 formed at the locations wherein the electrode tips 20 are to be formed, the electrode tips 20 can be electroplated to a predetermined length as previously described with reference to FIG. 4N. This can involve the deposition of an electroplating seed layer on a surface of each electrode seat 18 to initiate (i.e. seed) the electroplating, or for use in improving the adhesion of the electroplated electrode tips 20 to the electrode seats 18. Once the electroplating of the electrode tips 20 has been completed as shown in FIG. 5B, the patterned mask 56 can be removed (e.g. with a solvent such as acetone or a commercial photoresist remover) to leave the electrode tips 20 permanently attached to the electrode seats 18 as shown in FIG. 5C. Removing the layers of the sacrificial material 38 by selective etching then releases the electrodes 12 for movement and completes the formation of the electrode array 10.

Although the electrode tips 20 are shown being formed on an underside of the electrode seats 18 in FIGS. 5A–5C, those skilled in the art will understand that the electrode tips 20 can also be formed on a topside of the electrode seats 18. This can be done, for example, by etching an opening down through the layers of the sacrificial material 38 at a center of each electrode seat 18 to expose the silicon nitride layer 24 covering the electrode seat 18, or by etching the opening down to the surface of each electrode seats 18. Then, an electroplating seed layer can be deposited in each opening on the silicon nitride layer 24 or on the exposed surface of each electrode seat 18. A patterned mask 56 can then be provided over the sacrificial material 38, with a plurality of openings 58 therein at the locations where each electrode tip 20 is to be formed. The electrode tips 20 can then be electroplated to fill the openings 58; and the patterned mask 56 and the layers of the sacrificial material 38 can be removed to complete the electrode array 10.

In yet other embodiments of the present invention, the electrode array 10 can be formed with the electrode tips 20 comprising the semiconductor substrate material (e.g. silicon). This can be done by utilizing the process steps described previously with reference to FIGS. 4A–4I and then utilizing a series of substitute process steps described hereinafter with reference to FIGS. 6A–6F.

Figure 6A:
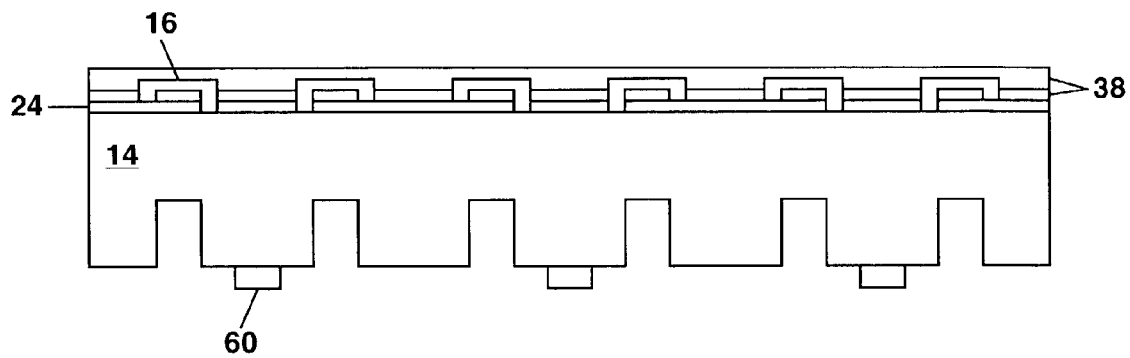
FIGS. 6A–6F illustrate the fabrication of additional embodiments of the present invention beginning after the process step described with reference to FIG. 4I.

In FIG. 6A, a patterned etch mask 60 can be provided on the backside of the substrate 14 at the locations where each electrode tip 20 is to be formed. The etch mask 60 can be formed by re-patterning the etch mask 42 in FIG. 4I, or alternately by removing the etch mask 42 in FIG. 4I and providing a new patterned etch mask.

Figure 6B:
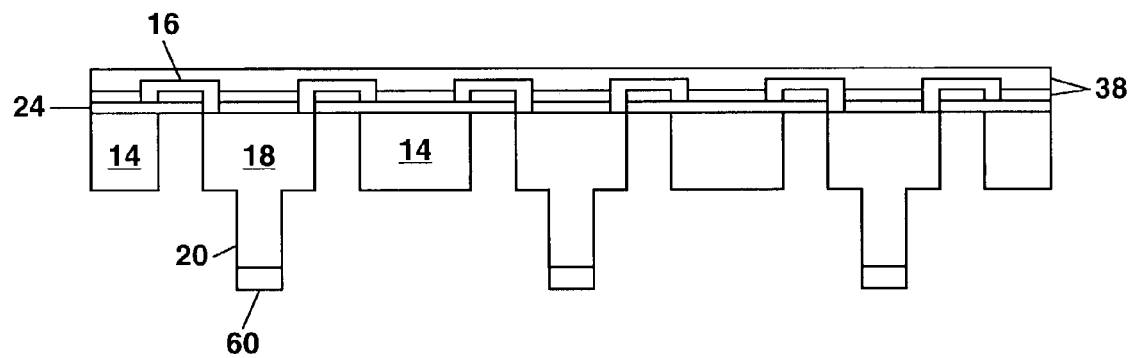

In FIG. 6B, a the substrate 14 can be etched completely through to separate the electrode seats 18 from the remainder of the substrate 14, and to define the shape of the electrode tips 20. This etching step can utilize the Bosch process as described previously.

Figure 6C:
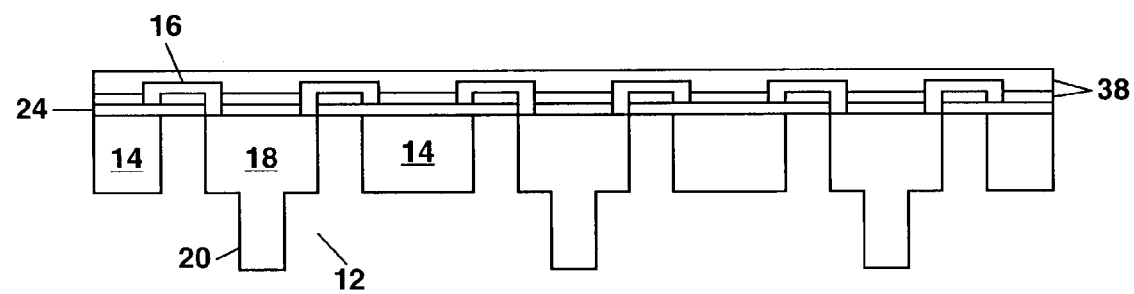

In FIG. 6C, the etch mask 60 can be removed (i.e. stripped). At this point, the layers of the sacrificial material 38 can be etched away as described previously to release the individual electrodes 12 for movement, thereby completing an electrode array 10 in which the electrode seats 18 and electrode tips 20 are formed integrally from the semiconductor substrate material. Since the semiconductor substrate material is electrically conductive, the electrodes 12 in FIG. 6C are fully functional and suitable for certain applications.

In other embodiments of the present invention, a coating of a metal or metal oxide can be provided over the electrodes 12 in FIG. 6C for improved electrical conductivity. This can be done in different ways as described hereinafter.

Figure 6D:
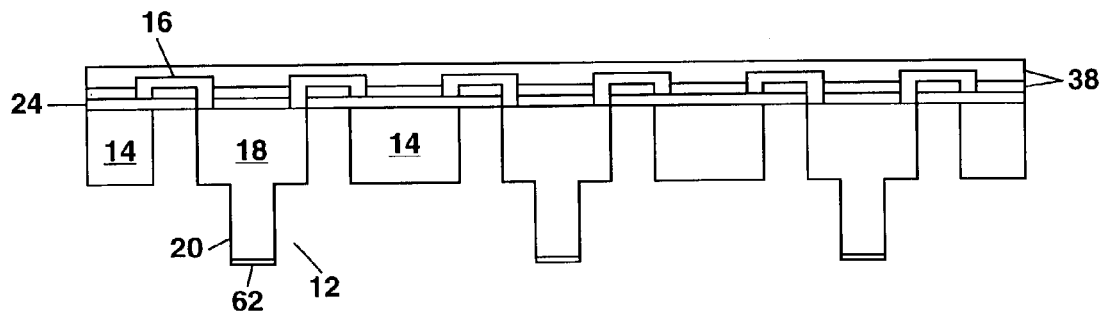

FIG. 6D shows a partial coating 62 of a metal (e.g. platinum, iridium, titanium, gold, or a combination thereof) or a metal oxide (e.g. iridium oxide) which can be provided over the exposed ends of the electrode tips 20, and which can also extend upward from the ends of the electrode tips 20 for a distance of, for example, 1–10 µm. Such a partial coating 62 can be formed, for example, by evaporation or sputtering, or by electroplating (e.g. by immersing the electrode tips 20 partway into a plating bath). An optional thermal oxidation step can be used, if needed, to convert an iridium metal coating 62 into an iridium oxide metal coating 62.

Once the partial coating 62 has been formed over the electrode tips 20, the silicon nitride layer 24 can be etched away underneath the springs, and the layers of the sacrificial material 38 can be removed as described previously. This releases the electrodes 12 for movement.

Figure 6E:
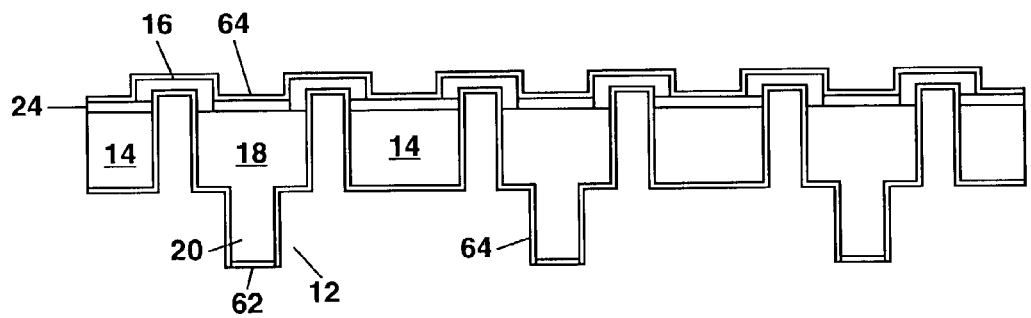

An optional electrically-insulating biocompatible coating 64 (e.g. parylene, silicon dioxide or silicon nitride) can be provided over the entire electrode array 10 using a conformal deposition process (e.g. LPCVD or VDP) as described previously. The coating 64 can then be removed from over the partial coating 62 as shown in FIG. 6E (e.g. by laser ablation, selective etching or solvent dissolution).

Figure 6F:
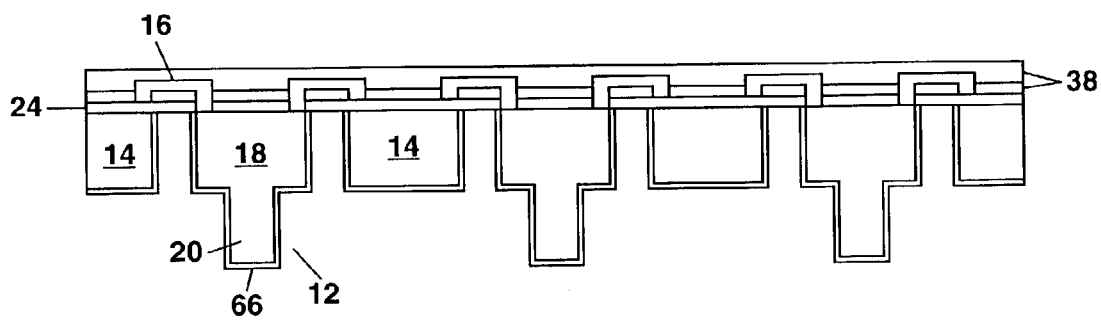

FIG. 6F shows a full-surface coating 66 of a metal or metal oxide formed over the exposed portions of the electrode seats 18 and electrode tips 20. The full-surface coating 66, which can be deposited by evaporation or sputtering, or alternately electroplated, can comprise a metal such as platinum, iridium, titanium or gold, or a combination thereof. An iridium oxide full-surface coating 66 can be formed, for example, by first depositing or electroplating an iridium coating 66 and then thermally oxidizing at least a portion of the iridium to form iridium oxide.

Once the full-surface coating 66 has been formed and the layers of the sacrificial material 38 have been removed, an optional electrically-insulating biocompatible coating 64 can be provided over the entire electrode array 10 and then removed from the ends of the electrode tips 20 as previously described with reference to FIG. 6E.

The electrode array 10 of the present invention can be used in conjunction with electronic circuitry 110 (e.g. neural stimulation circuitry which forms a part of a neural prosthesis such as an implantable retinal prosthesis) which can be formed on a separate substrate. The electronic circuitry 110, which can include a plurality of interconnected transistors and one or more photodetectors, can be electrically connected to the electrode array 10 through a plurality of wires, or be directly attached to the electrode array 10 as shown in FIG. 7.

Figure 7:
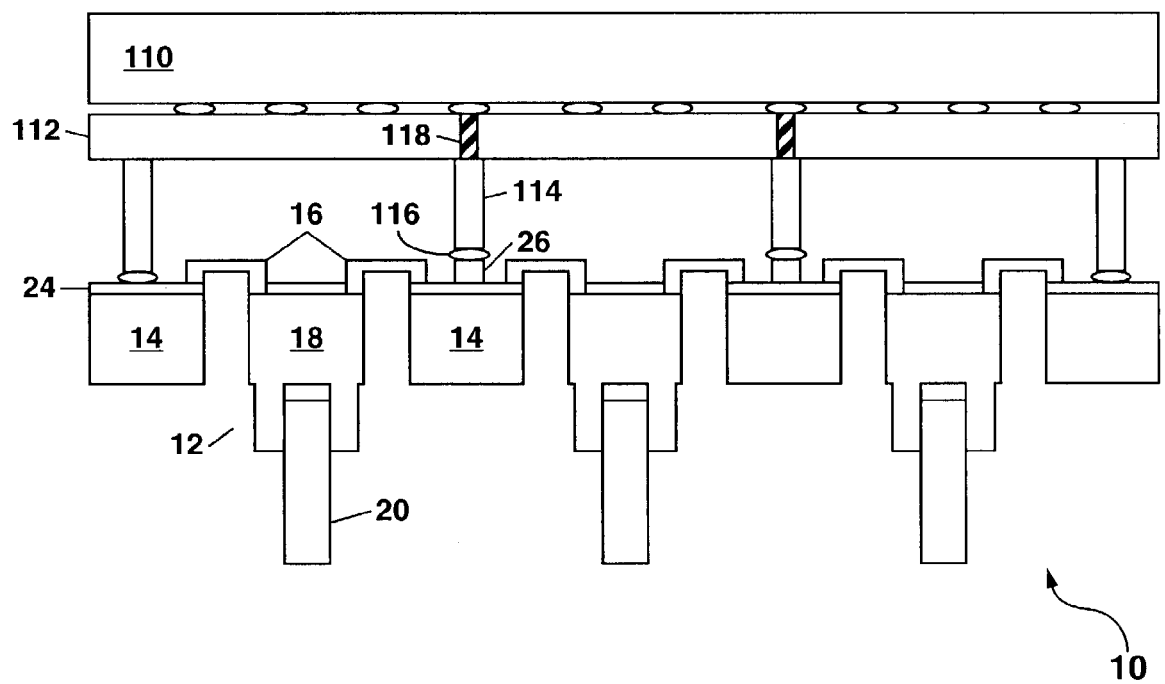
FIG. 7 illustrates an embodiment of the present invention wherein electronic circuitry is attached to the electrode array of FIGS. 1 and 2A–2B.

FIG. 7 schematically illustrates in cross-section view the attachment of electronic circuitry 110 to the electrode array 10. This can be done using an intermediary substrate 112 which includes a plurality of electrically-conductive posts 114 that can be aligned to features (e.g. the addressing circuitry 26 or bond pads 32) on the electrode array 10 and attached thereto using a plurality of solder bump bonds 116, or an electrically-conductive adhesive.

The intermediary substrate 112 can comprise, for example, a semiconductor substrate 112 that has been bulk micromachined to shape, or a substrate 112 whereon the electrically-conducting posts 114 are formed by LIGA to protrude outward from the substrate 112 or to extend therethrough, or a ceramic substrate 112, etc. The essential characteristic of the intermediary substrate 112 is that it provides a plurality of electrical connections between the electronic circuitry 110 (e.g. an integrated circuit chip) and the electrode array 10 while holding these two parts together. Electrically-conducting vias 118 can be provided through the intermediary substrate 112, as needed, to provide electrical conduction paths from a top surface of the substrate 112 to an underside thereof where the electrically-conducting posts 114 are located.

Once the electronic circuitry 110 has been attached to the electrode array 10 to form the apparatus shown in FIG. 7, the apparatus can be optionally coated for biocompatibility when this is needed (e.g. for forming a neural prosthesis). This biocompatibility can be provided, for example, by a conformal coating of parylene using VDP as described previously. Since the parylene can be deposited from a vapor at room temperature, all surfaces of the electronic circuitry 110, intermediary substrate 112, electrode array 10, solder bump bonds 116, external wiring (not shown), etc., can be provided with a biocompatible coating of parylene that can be, for example, up to 0.1 µm thick or more.

Figure 8A:
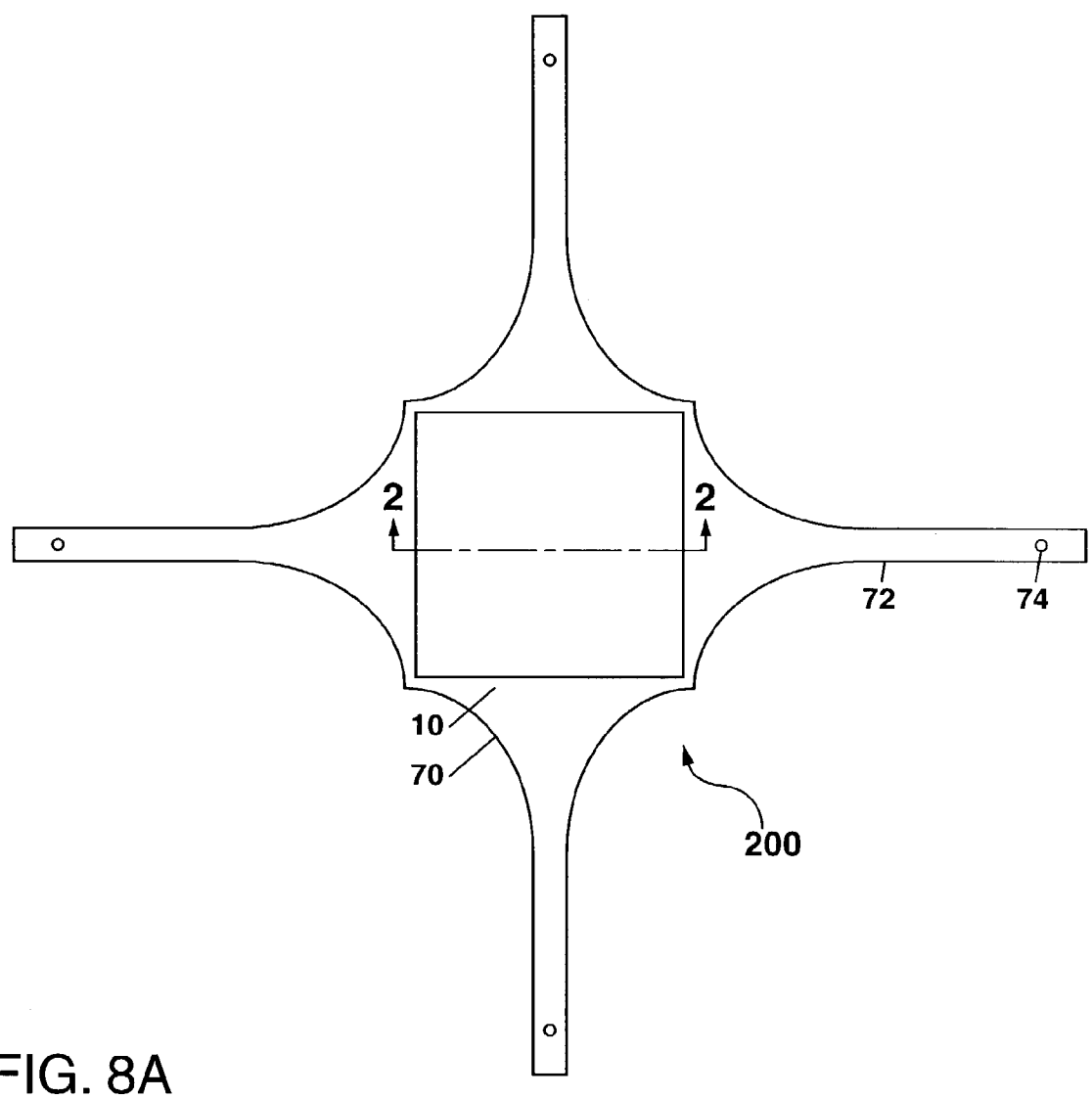
FIG. 8A shows a schematic plan view of the electrode array of the present invention with a flexible frame attached thereto for use in forming a portion of an implantable retinal prosthesis.
Figure 8B:
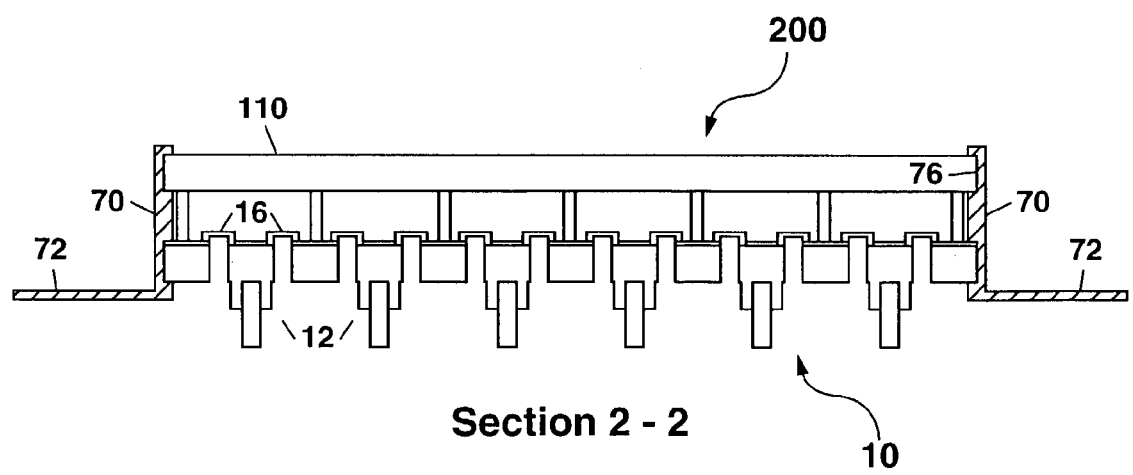
FIG. 8B shows a schematic cross-section view of the electrode array with the attached flexible frame along the section line 2—2 in FIG. 8A.

The electrode array 10 of the present invention can further include a flexible frame 70 attached to the substrate 14 for use in handling the electrode array 10, or for attaching the electrode array 10 onto a surface (e.g. a neural surface such as the epiretinal surface) to be electrically contacted by the electrode array 10. One example of such a flexible frame 70 for use with the electrode array 10 for use in an implantable retinal prosthesis 200 is schematically illustrated in FIGS. 8A and 8B. Although not shown in FIGS. 8A and 8B, the flexible frame 70 can optionally include electrical wiring (e.g. for forming a plurality of electrical connections to additional electronic circuitry not directly attached to the electrode array 10).

In the schematic plan view of FIG. 8A and the cross-section view of FIG. 8B, the flexible frame 70 can be attached to the electrode array 10 and to any electronic circuitry 110 that is directly attached to the electrode array 10 to form the implantable retinal prosthesis 200. The flexible frame 70 can include one or more wings 72 which extend outward from the electrode array 10, with each wing 72 including one or more through-holes 74 for use in attaching the flexible frame 70 and electrode array 10 to an epiretinal surface 130 shown in FIG. 9B.

Further details of the flexible frame 70 can be seen in FIG. 8B which shows a schematic cross-section view along the section line 2—2 in FIG. 8A. In FIG. 8B, the flexible frame 70 can be attached to the electrode array 10 at an outer edge thereof, and can further be attached to the outer edge of any electronic circuitry 110 included with the electrode array 10. The flexible frame 70 can comprise a biocompatible polymer such as PDMS that can be molded into shape and cured (e.g. at an elevated temperature of about 80° C. for one hour in the case of PDMS). The flexible frame 70 can include one or more recesses 76 adapted to receive and secure the electrode array 10 and any electronic circuitry 110 at the outer edges thereof. Alternately, the flexible frame 70 can be molded around the outer edges electrode array 10 and any electronic circuitry 110 and can optionally cover a topside of the electronic circuitry 110.

Figure 9A:
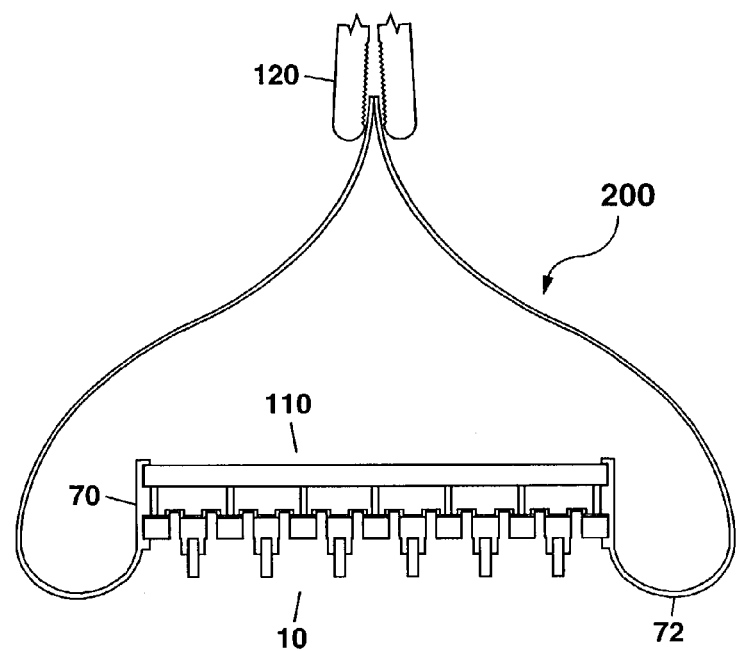
FIG. 9A schematically illustrates use of the flexible frame for handling and positioning the electrode array in preparation for implanting the electrode array as part of a retinal prosthesis.

The flexible frame 70 provides a convenient way of handling the electrode array 10 and any electronic circuitry 110 during implant surgery when these elements form a part of an implantable retinal prosthesis 200. For implantation of the retinal prosthesis 200, the wings 72 can be folded as shown in FIG. 9A to allow manipulation of the assembled electrode array 10 and electronic circuitry 110 by a surgeon using a an insertion tool 120 (e.g. a pair of forceps, or a specially-designed tool) which grasps and holds the ends of each wing 72. This allows the retinal prosthesis 200 to be inserted through a surgical incision in a patient's eye with minimal concern about damaging the electrode array 10 or the patient's eye.

Figure 9B:
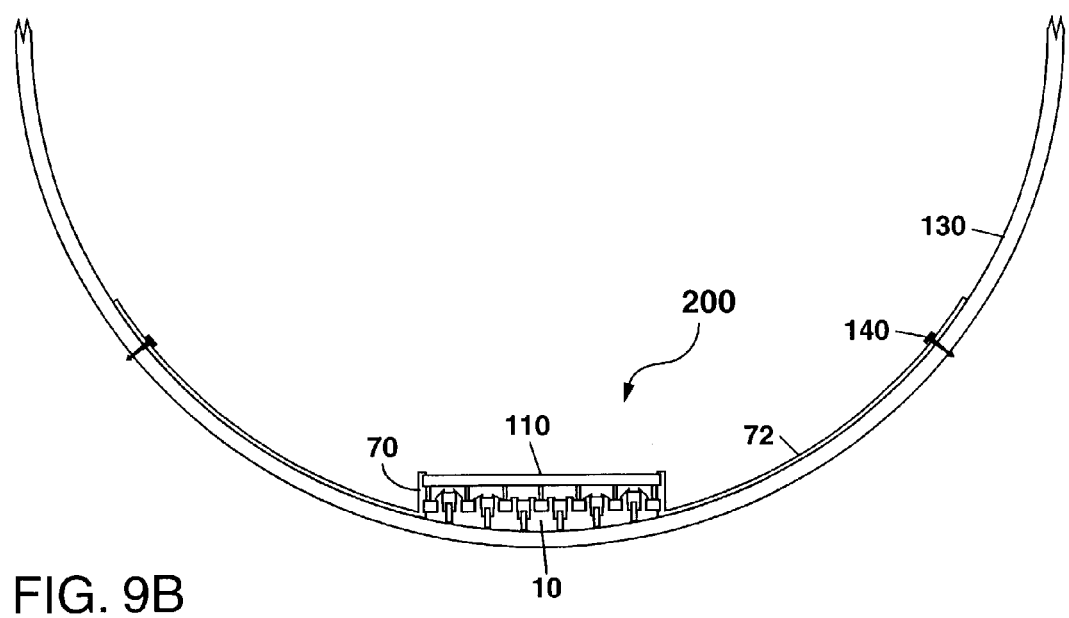
FIG. 9B schematically illustrates the positioning of the electrode array on an epiretinal surface and attaching the electrode array thereto.

Once the electrode array 10 and other intraocular portions of the retinal prosthesis 200 have been implanted into a patient's eye using conventional ophthalmic surgical techniques and positioned near the epiretinal surface 130, the wings 72 which have been secured by the insertion tool 120 can be released and allowed to unfold thereby aiding in placement and of the retinal prosthesis 200. This is schematically illustrated in FIG. 9B. The resiliency of the wings 72 can also help to urge the electrode array 10 into contact with the epiretinal surface 130.

Once the retinal prosthesis is in place as shown in FIG. 9B, each wing 72 can be secured to the epiretinal surface 130 using one or more sutures, or with a titanium tack 140 inserted in each through-hole 74. Each titanium tack 140 can pierce the retina, choroid and sclera to hold the electrode array 10 in place against the epiretinal surface 130. The ability of each electrode 12 in the array 10 to move independently upon a plurality of springs 16 allows the electrode array 10 to gently conform to the curvature of the epiretinal surface 130 while at the same time allowing each individual electrode 12 to maintain substantially the same low contact force on the epiretinal surface 130.

Operation of the retinal prosthesis 200 can utilize a radio-frequency (rf) antenna or alternately a photodetector located within the eye and connected to the electronic circuitry 110 for powering the electronic circuitry 110 and for providing visual information to the electronic circuitry 110 and the electrode array 10. The rf antenna and receiving electronic circuitry, which are not shown in FIGS. 9A and 9B, can be located remotely from the electronic circuitry 110 and connected thereto using flexible wiring. The rf antenna, receiving electronic circuitry and flexible wiring can all be folded up within the folded wings 72 in FIG. 9A to facilitate implanting of the retinal prosthesis 200 in a patient's eye. When the wings 72 are released as shown in FIG. 9B, the rf antenna, receiving electronic circuitry and flexible wiring cab unfold and assume a position in the patient's eye away from the electrode array 10 to help alleviate power dissipation and tissue heating concerns which might otherwise occur if the antenna and receiving circuitry were directly located on the electrode array 10.

The retinal prosthesis 200 generally provides a balanced biphasic stimulation (i.e. a positive current pulse paired with a slightly-delayed negative current pulse of equal and opposite charge) through the electrode array 110 to the underlying ganglion cells in the retina since this provides a needed electrical stimulation required for visual perception while eliminating any net charge accumulation on the electrodes 12 that might otherwise lead to electrochemical reactions and possible dissolution of the electrodes 12 in the array 10. The electrical stimulation provided through the electrode 12 to the underlying ganglion cells in the retina can be on the order of up to a few microamperes current with a pulse width of, for example, 0.1–2 milliseconds and a pulse repetition rate of up to several tens of Hertz. The electrical stimulation requirements for other types of neural tissue can be learned from practice of the present invention.

Figure 10A:
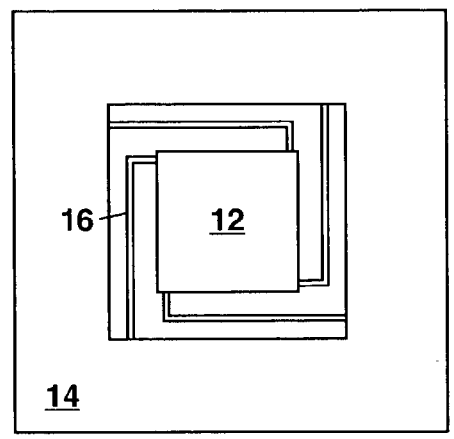
FIGS. 10A–10D schematically illustrate in plan view alternative designs for the springs and electrodes in forming other embodiments of the electrode array of the present invention.
Figure 10B:
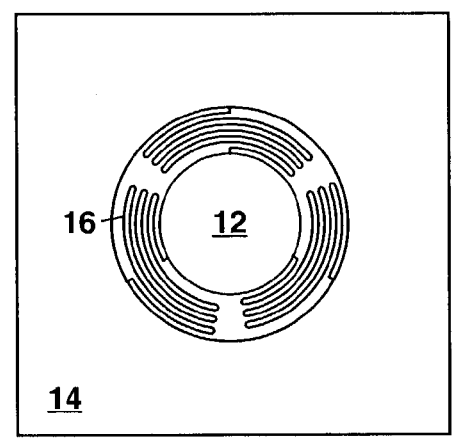
Figure 10C:
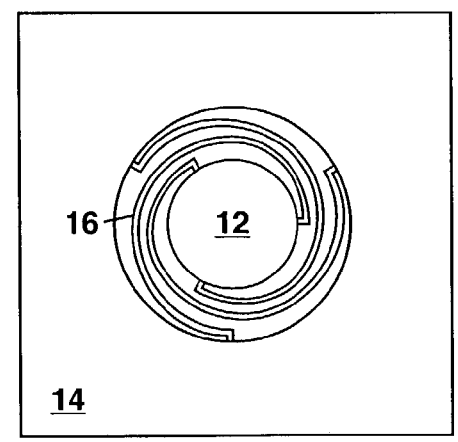
Figure 10D:
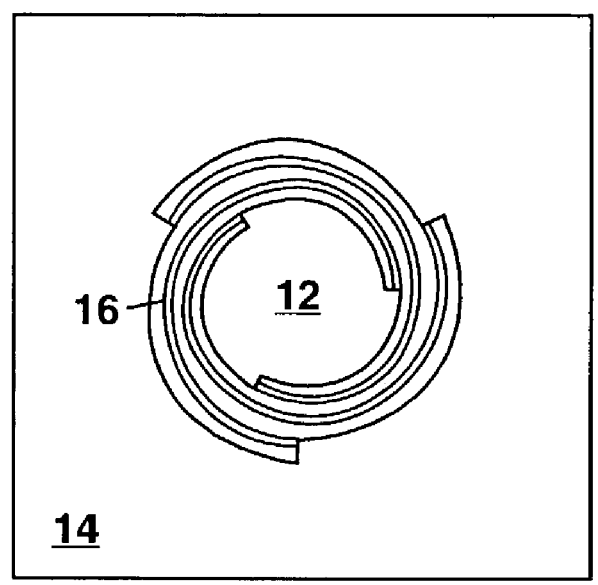

In other embodiments of the present invention, the springs 16 in the electrode array 10 can be formed from other electrically-conductive materials (e.g. metals), and can have other shapes as shown in the examples of FIGS. 10A–10D. In FIG. 10A, the springs 16 comprise folded springs 16, but with a single 90° fold for each spring 16. In FIG. 10B, the springs 16 can be folded about a circular electrode seat with each folded spring 16 comprising a plurality of arcuate sections connected together by folds at the ends thereof. In FIG. 10C, each spring 16 can be curved with optional 900 folds where the spring 16 is attached to the substrate 14 and to the electrode 12. In FIG. 10D, each spring 16 can be formed as a curved spring without any folds if the electrode 12 and substrate 14 are shaped as shown. FIGS. 10A–10D are provided as examples and are not intended to limit the present invention in any way. Those skilled in the art will understand that there are many other ways of forming the plurality of springs 16; and that the electrodes can have an arbitrary shape (e.g. circular, square, polygonal, etc.).

Although the electrode array 10 of the present invention has been described in relation to use in an implantable retinal prosthesis 200, those skilled in the art will understand that the electrode array 10 described herein has applications for use in stimulating or sensing many different types of neural tissue including neural tissue associated with visual, auditory and sensory systems and neural tissue associated with the control of particular muscles (e.g. for bladder function or the activation of paretic limbs) or organs. Other applications and variations of the present invention will become evident to those skilled in the art. For example, other embodiments of the electrode array 10 of the present invention can be formed with the individual electrodes 12 being pointed for piercing neural tissue. Such pointed electrodes 12 can be formed by etching or electroforming. The matter set forth in the foregoing description and accompanying drawings is offered by way of illustration only and not as a limitation. The actual scope of the invention is intended to be defined in the following claims when viewed in their proper perspective based on the prior art.

What is claimed is:

1. A micromachined electrode array comprising a plurality of spaced-apart electrodes attached to a supporting substrate and protruding outward substantially normal to a surface of the substrate, with each electrode being flexibly attached at one end thereof to the substrate by a plurality springs.

2. The electrode array of claim 1 wherein the substrate comprises a semiconductor material.

3. The electrode array of claim 2 wherein the electrodes comprise the semiconductor material.

4. The electrode array of claim 2 wherein the electrodes comprise an electrically conductive material selected from the group consisting of silicon, platinum, titanium, gold, iridium, iridium oxide and combinations thereof.

5. The electrode array of claim 1 wherein a majority of each electrode is overcoated with an electrically-insulating material.

6. The electrode array of claim 5 wherein the electrically-insulating material is selected from the group consisting of parylene, silicon nitride, silicon dioxide and combinations thereof.

7. The electrode array of claim 1 wherein each electrode is moveable over a distance of up to 500 microns.

8. The electrode array of claim 1 wherein the springs comprise folded springs.

9. The electrode array of claim 1 wherein a spring constant of each spring in the electrode array is substantially the same.

10. The electrode array of claim 1 wherein a spring constant of the springs attached to a first electrode is different from the spring constant of the springs attached to a second electrode.

11. The electrode array of claim 1 wherein each electrode provides a contact force that is substantially the same when the electrode array is urged into contact with a curved surface.

12. The electrode array of claim 1 further comprising wiring on the substrate for electrically addressing each electrode.

13. The electrode array of claim 1 further comprising means for sensing a contact force for at least one of the plurality of electrodes when the electrode array is urged into contact with a surface.

14. A micromachined electrode array, comprising:
    (a) a semiconductor substrate; and
    (b) a plurality of spaced-apart electrodes formed, at least in part, from the substrate, with each electrode being attached to the substrate by a plurality of springs to provide for movement of the electrode in a direction substantially normal to the substrate.

15. The electrode array of claim 14 wherein the substrate comprises silicon.

16. The electrode array of claim 14 wherein each electrode comprises a base portion formed from the substrate, and an elongate metal portion attached to the base portion.

17. The electrode array of claim 16 wherein each electrode is further overcoated with an electrically-insulating material except for an end of the metal portion distal to the base portion.

18. The electrode array of claim 14 wherein each electrode is overcoated with a metal or an electrically-conducting metal oxide.

19. The electrode array of claim 18 wherein a majority of each electrode is further overcoated with an electrically-insulating material.

20. The electrode array of claim 14 wherein each spring comprises a folded spring.

21. The electrode array of claim 14 wherein each electrode provides a contact force that is substantially the same when the electrode array is urged into contact with a curved surface.

22. The electrode array of claim 14 wherein the substrate includes electrical wiring for providing an electrical connection to each electrode in the electrode array.

23. The electrode array of claim 14 further comprising a flexible frame attached to the substrate for positioning of the electrode array, or for attachment of the electrode array to a surface.

24. The electrode array of claim 14 further comprising means for sensing a contact force for at least one of the plurality of electrodes when the electrode array is urged into contact with a surface.

25. A micromachined electrode array, comprising:
   (a) a silicon substrate;
   (b) a plurality of spaced-apart bulk-micromachined electrode seats formed from the substrate;
   (c) a plurality of surface-micromachined springs formed in a polysilicon layer deposited over the substrate, with each surface-micromachined spring being attached at one end thereof to the substrate, and at the other end thereof to one of the plurality of bulk-micromachined electrode seats; and
   (d) an elongate electrode attached to or formed integrally with each bulk-micromachined electrode seat, with the electrode being oriented in a direction substantially normal to the substrate.

26. The electrode array of claim 25 wherein each electrode comprises a metal.

27. The electrode array of claim 25 wherein each electrode comprises a metal coating formed thereon.

28. The electrode array of claim 25 wherein each electrode comprises a coating of an electrically-conductive metal oxide.

29. The electrode array of claim 25 wherein a majority of each electrode is overcoated with an electrically-insulating material.

30. The electrode array of claim 25 wherein each spring comprises a folded spring.

31. The electrode array of claim 25 wherein the springs attached to each electrode seat are adapted to provide a spring constant which is inversely proportional to a displacement of the electrode seat whereon the springs are attached when the electrode array is urged into contact with a curved surface.

32. The electrode array of claim 25 further comprising electrical wiring on the substrate for providing an electrical connection to each electrode in the electrode array.

33. The electrode array of claim 25 further comprising a flexible frame attached to the substrate for handling of the electrode array, or for attaching the electrode array onto a surface to be electrically contacted by the electrode array.

34. The electrode array of claim 25 further comprising means for sensing a contact force for at least one electrode of the electrode array when the electrode array is urged into contact with a surface.

35. An electrode array for neural stimulation, comprising:
   (a) a silicon substrate; and
   (b) a plurality of electrodes arranged in an array and protruding outward from a surface of the substrate, with each electrode comprising silicon and being flexibly attached to the substrate by a plurality of springs comprising polysilicon.

36. The electrode array of claim 35 wherein each electrode has a width of 100 microns or less.

37. The electrode array of claim 35 wherein each electrode has a length of one millimeter or less.

38. The electrode array of claim 35 wherein each electrode is overcoated with a metal or an electrically-conducting metal oxide.

39. The electrode array of claim 38 wherein a majority of each electrode is further overcoated with an electrically-insulating biocompatible material.

40. The electrode array of claim 35 wherein each electrode is overcoated with an electrically-conductive material selected from the group consisting of titanium, gold, platinum, iridium, iridium oxide and combinations thereof.

41. The electrode array of claim 40 wherein a majority of each electrode is further overcoated with an electrically-insulating biocompatible material.

42. The electrode array of claim 35 wherein each spring comprises a folded spring.

43. The electrode array of claim 35 wherein each electrode provides a contact force that is substantially the same when the electrode array is urged into contact with a curved neural surface for electrical stimulation thereof.

44. The electrode array of claim 35 further comprising electrical wiring formed on the substrate for providing an electrical connection to each electrode in the electrode array.

45. The electrode array of claim 35 further comprising a flexible frame attached to the substrate for positioning of the electrode array to contact a neural surface for electrical stimulation thereof, or for attachment of the electrode array to the neural surface.

46. The electrode array of claim 35 further comprising means for sensing a contact force for at least one of the plurality of electrodes when the electrode array is urged into contact with a neural surface.

* * * * *